US010857192B2

(12) United States Patent
Elmann et al.

(10) Patent No.: US 10,857,192 B2
(45) Date of Patent: Dec. 8, 2020

(54) ANTI-NEUROINFLAMMATORY AND ANTIOXIDATIVE EFFECTS OF PI INFUSION— IMPLICATIONS FOR NEURODEGENERATIVE DISEASES

(71) Applicant: THE STATE OF ISRAEL, MINISTRY OF AGRICULTURE & RURAL DEVELOPMENT, AGRICULTURAL RESEARCH ORGANIZATION (ARO) (VOLCANI CENTER), Bet-Dagan (IL)

(72) Inventors: Anat Elmann, Rehovot (IL); Rivka Ofir, Moshav Hazeva (IL)

(73) Assignee: THE STATE OF ISRAEL, MINISTRY OF AGRICULTURE & RURAL DEVELOPMENT, AGRICULTURAL RESEARCH ORGANIZATION, Bet-Dagan (IL)

( * ) Notice: Subject to any disclaimer, the term of this patent is extended or adjusted under 35 U.S.C. 154(b) by 598 days.

(21) Appl. No.: 14/655,342

(22) PCT Filed: Dec. 24, 2013

(86) PCT No.: PCT/IL2013/051060
§ 371 (c)(1),
(2) Date: Jun. 25, 2015

(87) PCT Pub. No.: WO2014/102780
PCT Pub. Date: Jul. 3, 2014

(65) Prior Publication Data
US 2015/0359832 A1    Dec. 17, 2015

Related U.S. Application Data

(60) Provisional application No. 61/848,186, filed on Dec. 27, 2012.

(51) Int. Cl.
*A61K 36/28*    (2006.01)
(52) U.S. Cl.
CPC .................................... *A61K 36/28* (2013.01)
(58) Field of Classification Search
CPC ....................................................... A61K 36/28
USPC ................................................. 424/754, 778
See application file for complete search history.

(56) References Cited

U.S. PATENT DOCUMENTS

| | | |
|---|---|---|
| 2012/0018356 A1 | 1/2012 | Jalink |
| 2013/0325346 A1 | 12/2013 | McPeek |
| 2014/0127672 A1 | 5/2014 | Davis et al. |

OTHER PUBLICATIONS

Elmann et al "Antioxidant and Astroprotective Effects of a Pulicaria incisa Infusion" , Oxidative Medicine and Cellular Longevity, vol. 2012, Article ID 157598, 10 pages, Nov. 2012. (Year: 2012).*

Elmann et al "Antioxidant and Astroprotective Effects of a Pulicaria incisa Infusion", Oxidative Medicine and Cellular Longevity, vol. 2012, Article ID 157598, 10 pages, Nov. 2012. (Year: 2012) (Year: 2012).*

Antioxidant and astroprotective effects of a Pulicaria incisa infusion Oxid Med Cell Longev. 2012;2012:157598. Published online Dec. 23, 2012. doi: 10.1155/2012/157598 Anat Elmann, Alona Telerman, Sharon Mordechay, Hilla Erlank and Rivka Ofir Dec. 23, 2012 (Dec. 23, 2012) whole document.

"Sesquiterpenes from an Egyptian Herbal Medicine, Pulicaria undulate, with Inhibitory Effects on Nitric Oxide Production in RAW 264.7 Macrophage Cells" Chem. Pharm. Bull. 60 (3) 363-370 (2012) (Received Nov. 17, 2011; accepted Dec. 20, 2011; published online Jan. 6, 2012) Mahamed-Elamir F. Hegazy, Hisashi Matsuda, Seikou Nakamura, aMikuko Yabe, a Tomoko Matsumoto, and Masayuki Yoshikawa. Jan. 6, 2012 (Jan. 6, 2012).

Inflamation in neurodegenernative diseases Immunology. Feb. 2010; 129 (2):154-169. first published online: Jan. 7, 2010 Sandra Amor, Fabiola Puentes, David Baker and Paul van der Valk Jan. 7, 2010 (Jan. 7, 2010) whole document.

"Antioxidant properties and lipid profile of Diplotaxis harra, Pulicaria inciA and Avicennia marina" Acta Alimentaria, vol. 41 (2), pp. 143-151 (2012) DOI: 10.1556/AALIM.412012.2.1 (Received; Feb. 18, 2009; accepted: Nov. 9, 2011) W.Abd El-Gleel and M.F.R. Hassanien.

Mehdi Ravandeh et al: "Screening of chemical composition of essential oil, mineral elements and antioxidant activity in Pulicaria Undulata (L.) C. A. Mey from Iran",Journal of Medicinal Plants Research, Mar. 17, 2011 (Mar. 17, 2011), pp. 2035-2040, XP55289232,Retrieved from the Internet: URL:http://www.academicjournals.org/journal/JMPR/article-full-text-pdf/A146F2019778.

Ma Al-Yahya et al: "Potential Cancer Chemopreventive and Cytotoxic Agents From Pulicaria Crispa", Journal of Natural Products, Jan. 1, 1988 (Jan. 1, 1988), Jun. 1, 1988 (Jun. 1, 1988 ), pp. 621-624, XP55289327, EPO Form 1703 01.91TRI Datum Blatt Anmelde-Nr: D~e cf Form 1507 Sheet 2 Application 1 3 8 6 7 8 0 3 . 2 No: Date Feuille Retrieved from the Internet: URL:http://pubs.acs.org/doi/pdf/10.1021 /np50057a038.

Ali Sa: "Natural products as therapeutic agents for schistosomiasis", Research Journal of Medicinal Plant, Academic Journals Inc, US, vol. 5, No. 1, Jan. 1, 2011 (Jan. 1, 2011 ), pp. 1-20, XP009191001, ISSN: 1819-3455.

"Yellow bane", Pharmaceutical Journal 20030906 GB, vol. 271, No. 7265, Sep. 6, 2003 (Sep. 6, 2003), p. 304, XP009190996, ISSN: 0031-6873.

Harlev E et al: "Anticancer attributes of desert plants: A review", Anti-Cancer Drugs 2012 Lippincott Williams and Wilkins GBR, vol. 23, No. 3, Mar. 2012 (Mar. 2012), pp. 255-271, XP009190997, ISSN: 0959-4973.

(Continued)

*Primary Examiner* — Michael Barker
*Assistant Examiner* — Deborah A Davis
(74) *Attorney, Agent, or Firm* — Mark M. Friedman

(57) ABSTRACT

This invention relates to the use *Pulicaria incisa* (Pi) infusion for granting cells and tissues with anti-oxidative effect. The invention further relates to the use *Pulicaria incisa* (Pi) infusion for treating neuroinflammatory conditions. The invention further relates to cultivated Pi in treating neuroinflammatory conditions and producing anti-oxidative effect.

11 Claims, 19 Drawing Sheets

(56) References Cited

OTHER PUBLICATIONS

Mothana Ramzi A A et al: "Assessment of selected Yemeni medicinal plants for their in vitro antimicrobial, anticancer, and antioxidant activities", Pharmaceutical Biology, Swets and Zeitlinger, Lisse, NL, vol. 49, No. 2, Feb. 1, 2011 (Feb. 1, 2011 ), pp. 200-210, XP009190999, ISSN: 1388-0209.

Alghaity A A et al: "Anti-inflammatory effects of the chloroform extract of Pulicaria guestii ameliorated the neutrophil infiltration and nitric oxide generation in rats", Toxicology and Industrial Health, Princeton, NJ, US, vol. 27, No. 10, Nov. 1, 2011 (Nov. 1, 2011 ), pp. 899-910, XP009191000, ISSN: 0748-2337, DOI: 10.1177/0748233711399320.

Anat Elmann et al: "Antioxidant and astroprotective effects of a Pulicaria incisa infusion", Oxid Med Cell Longev. 2 012;, Dec. 23, 2012 (Dec. 23, 2012), p. 157598, XP055269649.

W. Aso El-Gleel and M.F.R. Hassanief "Antioxidant Properties and Lipid Profile of Diplotaxis Harra. Pulicaria INC/SA and Avicennia Marina"in ActaA/imentaria, vol. 41(2),pp.143-151 (2012) DOI:/0./556/AA/im.41.2012.2./.

Hussein Bakthira, Nasser A. Awadh Ali*b, NOrbeet arnoldc, Axel Teichertc , and Ludger Wessjohanne :"Anticholinesterase Activity of Endemic Plant Extracts From Soqotra" in Bakthir et at., Afr J Tradit Complement Altern Med. (2011) 8(3):296-299.

Sanaa Ahmed Ali;"Natural Products as Therapeutic Agents for Schistosomiasis"in Research Journal of Medicinal Plant 5 (1): 1-20, 2011 ISSN 1819-3455 I DOI: 10.3923/rjmp.2011.I.20 © Academic Journals. Inc.

Anat Elmann, Alona Telerman, Sharon Mordechay, Hilla Erlank Rivka Ofir, "Antioxidant and astroprotective effects of a Pulicaria incisa infusion Oxid Med Cell Longev", 2012; 2012: 157598. Dec. 23, 2012.

Mohamed- Elamir F. Hegazy, Hisashi Matsuda, Seikou Nakamura, Mikuko Yabe, Tomoko Matsumoto, and Masayuki Yoshikawa, "Sesquiterpenes from an Egyptian Herbal Medicine, Pulicaria undulate, with Inhibitory Effects on Nitric Oxide Production in RAW264.7 Macrophage Cells", Jan. 6 2012.

Sandra Amor, Fabiola Puentes, David Baker and Paulvan Der Valk, "Inflammation in neurodegenerative diseases" Immunology. Jan. 7, 2010.

W .ABD El-Gleel and M.F.R. Hassanien, "Antioxidant properties and lipid profile of Diplotaxis harra, Pulicaria incisa and Avicennia marina", 2012.

* cited by examiner

ANTI-NEUROINFLAMMATORY AND ANTIOXIDATIVE EFFECTS OF PI INFUSION— IMPLICATIONS FOR NEURODEGENERATIVE DISEASES

FIELD OF THE INVENTION

The invention relates to the use *Pulicaria incisa* (Pi) infusion for granting cells and tissues with anti-oxidative effect. The invention further relates to the use *Pulicaria incisa* (Pi) infusion for treating neuroinflammatory conditions.

DESCRIPTION OF THE STATE OF THE ART

The elevation in life span of the population in the western world caused an elevated frequency of neurodegenerative diseases, like Alzheimer's and Parkinson's disease. These diseases have multifactorial pathogenesis, and in most of them, a massive neuronal cell death occurs as a consequence of an uncontrolled neuroinflammatory response. This process plays a pivotal role in the initiation and progression of various neurodegenerative diseases and involves the activation of two main cell types in the brain—astrocytes and microglia (MG). These cells can produce proinflammatory cytokines (such as TNFα) and cytotoxic agents in response to ischemia, traumatic and infectious insults, leading to exaggeration of the disease processes. Inhibition of the activated cells may provide en effective therapeutic intervention that might alleviate the progression of the neurodegenerative diseases. One of the molecules secreted by these activated cells is nitric oxide (NO), which is a free radical that causes nitrosative stress that plays a role in neurodegenerative diseases. NO is a free radical which serves as a double-edged sword depending on its concentration in the microenvironment, and is involved in both physiological and pathological processes of many organ systems including the brain. Excessive amounts of NO are synthesized by induced NO-synthases (iNOS), secreted by both activated astrocytes and MG. Activation of iNOS and NO generation may serve as a marker and therapeutic target in ischemia, multiple sclerosis, spinal cord injury, Alzheimer's disease and inherited peroxisomal (e.g. X-linked adrenoleukodystrophy; X-ALD) and lysosomal (e.g. Krabbe's disease) disorders.

Compared with other tissues, the brain is particularly vulnerable to oxidative damage due to its high rate of oxygen utilization and the great deal of oxidizable polyunsaturated fatty acids it contains. In addition, certain regions of the brain are rich in iron, a metal that is catalytically involved in the production of damaging, reactive oxygen species (ROS). Although ROS are critical intracellular signaling messengers, an excess of free radicals may lead to peroxidative impairment of membrane lipids and, consequently, to the disruption of neuronal functions and apoptosis. The ROS known to be responsible for neurotoxicity are hydrogen peroxide ($H_2O_2$), superoxide anions ($O_2^-$) and hydroxyl radicals ($OH^-$).

Brain cells have the capacity to produce large quantities of peroxides, particularly H2O2. Excess H2O2 accumulates in response to brain injuries and during the course of neurodegenerative diseases and can cross cell membranes to elicit biological effects from inside the cells. Although H2O2 is generally not very reactive, it is thought to be the major precursor of highly reactive free radicals that may cause damage in the cell, through iron ion- or copper ion-mediated oxidation of lipids, proteins and nucleic acids. This capability can partially account for $H_2O_2$-mediated neuronal and glial death. $H_2O_2$ also induces differential protein activation, which accounts for its varied biological effects. In the mammalian central nervous system (CNS), the transition metal zinc is found only in the synaptic vesicles of glutamatergic neurons and plays a special role in modulating synaptic transmission. Chelatable zinc is released into the synaptic cleft with the neurotransmitter during neuronal execution. Under normal circumstances, the robust release of zinc is transient and the zinc is efficiently cleared from the synaptic cleft to ensure the performance of successive stimuli. However, under pathological conditions, elevated levels of extracellular zinc have been recognized as an important factor in neuropathology. In neurotransmission, the amount of zinc in the synaptic cleft is in the range of 10 to 30 µM, but, under pathological conditions that involve sustained neuronal depolarization (e.g., ischemia, stroke or traumatic brain injury), the concentration of extracellular zinc can increase to 100 to 400 µM, which can contribute to the resulting neuropathology. In vivo and in vitro studies have shown that at concentrations that can be reached in the mammalian CNS during excitotoxic episodes, injuries or diseases, zinc induces oxidative stress and ROS production, which contribute to the death of both glial cells and neurons. Zinc has been shown to decrease the glutathione (GSH) content of primary cultures of astrocytes, increase their GSSG content and inhibit glutathione reductase activity in these cells. Furthermore, it slows the clearance of exogenous $H_2O_2$ by astrocytes and promotes intracellular production of ROS. Thus, ROS generation, glutathione depletion and mitochondrial dysfunction may be key factors in $ZnCl_2$-induced glial toxicity.

Oxidative stress has emerged as a major mechanism that underlies the etiology of a variety of neuropathological disorders, including ischemic stroke, traumatic brain injury (TBI), depression, Alzheimer's disease, Parkinson's disease.

Inflammatory bowel disease (IBD) is a chronic condition of the intestine involving inflammatory processes, and the major types are Crohn's disease and ulcerative colitis.

Oxidative stress, caused by reactive oxygen species (ROS), is a major contributor to inflammatory bowel disease (IBD)-associated neoplasia. The most compelling evidence in support of the causal relationship between inflammation and carcinogenesis is provided by ulcerative colitis (UC)-associated colorectal cancer (UC-CRC) and tumors arising as a consequence of Crohn's disease and hepatitis C infection. Indeed, inflammation is regarded as the seventh hallmark of cancer.

The role of ROS is of major importance, particularly as oxidative stress is one of the most important pathogenetic factors in ulcerative colitis (UC)-associated colorectal cancer (UC-CRC). Amongst the immune regulatory factors, reactive oxygen species (ROS) are produced in abnormally high levels in IBD. Their destructive effects may contribute to the initiation and/or propagation of the disease.

IL-6 is a multifunctional cytokine produced mainly by cells of the immune system. Although IL-6 expression has been implicated, n the pathogenesis of a variety of diseases including glomerulunephritis, multiple myeloma, rheumatoid arthritis, and cardiac myxoma, IL-6 predominantly detected in Crohn's disease and ulcerative colitis specimens of the inflammatory samples. Serum IL-6 level correlates with the disease state as the level decreases upon improvement of the disease condition, and returns to the control level when inflammation in the gut subsides. Moreover, in colitis-associated cancer which is the most serious complication of inflammatory bowel disease, IL-6 plays a critical tumor promoter during early tumorigenesis by enhancing proliferation and survival of normal and premalignant intestinal epithelial cells.

Astrocytes are the most abundant type of glial cell in the brain and play multiple roles in the protection of brain cells. Under ischemic conditions, astrocytes can remove excess glutamate and $K^+$ to protect neurons from glutamate-mediated cytotoxicity and depolarization. Astrocytes can also supply energy and promote neurogenesis and synaptogenesis in response to ischemia-induced brain damage. Astrocytes release multiple neurotrophic factors, such as Glial derived neurotrophic factor (GDNF), to protect themselves and neighboring cells from in vitro ischemia and there is evidence that dysfunctional astrocytes can enhance neuronal degeneration by decreasing the secretion of trophic factors. GDNF can promote the survival of substantia nigra dopaminergic neurons, induce neurite outgrowth and sprouting, up-regulate tyrosine hydroxylase expression and enhance synaptic efficacy. Moreover. GDNF has been shown to protect cultured astrocytes from apoptosis after ischemia by inhibiting the activation of caspase-3.

The study of astrocytes is particularly important in light of the co-existence of apoptotic death of neurons and astrocytes in brains affected by ischemia and neurodegenerative diseases. Despite their high levels of antioxidative activity, astrocytes exhibit a high degree of vulnerability and are not resistant to the effects of ROS. They respond to substantial or sustained oxidative stress with increased intracellular $Ca^{2+}$, loss of mitochondrial potential and decreased oxidative phosphorylation. Since astrocytes determine the brain's vulnerability to oxidative injury and form a tight functional unit with neurons, impaired astrocytic energy metabolism and antioxidant capacity and the death of astrocytes may critically impair neuronal survival. Thus, protection of astrocytes from oxidative stress appears essential for the maintenance of brain function.

Both astrocytes and microglial cells can produce proinflammatory cytokines (such as Tumor necrosis factor alpha, TNFα) and cytotoxic agents in response to ischemia, traumatic and infectious insults, chronic neurodegenerative diseases leading to deterioration of the disease processes.

It is known that some cytokines are involved in the up and down regulation of immune and inflammatory cells, and in regulation of activity in connective tissue and neural, epithelial, endothelial, and other cell types which are involved in tissue repair and restoration of homeostasis.

Based on the pathophysiological roles of astrocytes in ischemic brains, it appears that astrocyte damage causes impairment of brain function during cerebral ischemia. In recent years, there has been an increased interest in plants as a source of bioactive substances that might be developed as potential nutraceuticals and various activities of such substances have been demonstrated in in vitro and in vivo experimental systems. Several studies have shown that some herbal medications and antioxidants show promise toward preventing Alzheimer's disease.

Glutamate Toxicity. Glutamate-evoked excitotoxicity has been implicated in the etiology of many neurodegenerative diseases including Alzheimer's disease, Parkinson's disease, and ischemic stroke. ROS provoked by glutamate-linked oxidative stress plays crucial role in the pathogenesis of these disorders.

*Pulicaria incisa* (Pi) is a desert plant that belongs to the Asteraceae family and has been used for many years in traditional medicine for the treatment of heart disease and as a hypoglycemic agent. Pi has been found to contain high amount of unsaturated fatty acids, to decrease total lipid, total cholesterol and triglyceride levels and has been proposed as a potential hypocholesterolemic agent.

Ramadan at al., J. Verbr. Lebensm. (2009) 4:239-245, examined the antioxidant properties of the methanolic extracts of Pi. Ramadan et al. did not demonstrate any anti-oxidant activity of the infusion of Pi. Moreover, Ramadan et al. showed a mere in vitro biochemical inhibition of the oxidation of linoleic acid by methanolic extract of Pi in a cell-free system and not a protection of living cells. Ramadan did not show any effects of Pi in the context of neurodegenerative diseases.

It is almost impossible commercialize the Pi or the Pi infusion by collecting the plant from its natural habitat. For commercialization purposes, plants should be grown in large masses under constant conditions so they could serve as a more available source of the active phytochemicals.

According to Gudaityte et al., *Biochemical Systematics and Ecology* 35 (2007) 582-592, data obtained clearly indicate the presence of a remarkable chemical polymorphism within the population of *A. millefolium* transferred from 14 different locations in Lithuania.

In Rahimmalek et al., *Industrial Crops and Products*, Volume 29, Issues 2-3, March 2009, Pages 348-355, compositions of essential oils of 19 accessions belonging to six different *Achillea* species, transferred from the natural habitats in 10 provinces to field conditions, were assessed. Results indicated a significant variation in oil composition among and within species.

Rivas-Ubach et al., *Proc Natl Acad Sci USA*, 2012 Mar. 13; 109(11):4181-6 teach that shifts in the elemental stoichiometry of organisms in response to their ontogeny and to changing environmental conditions should be related to metabolomic changes because elements operate mostly as parts of molecular compounds. Rivas-Ubach et al. show this relationship in leaves of *Erica multiflora* in response to moderate experimental field conditions of drought and warming. The N/P ratio in leaves decreased in the metabolically active growing seasons, coinciding with an increase in the content of primary metabolites. These results support the growth-rate hypothesis that states that rapidly growing organisms present low N/P ratios because of the increase in allocation of P to RNA.

A salt-induced improvement in the biosynthesis of secondary metabolites was also described in *Rosmarinus officinalis* (Renee et al., *Phytochemistry.* 1996 November; 43(5):1033-9).

Wang et al. (*Chemistry & Riodiversity*, Vol. 7 (2010)) disclose that comparison of seven ginsenosides in wild and cultivated American ginseng revealed that with respect to ginsenosides ratio, there is a significantly large difference between cultivated a wild American ginseng. Wang suggests that wild American ginseng may have distinct pharmacological activities and therapeutic effects compared to the cultivated.

It may be assumed that the extreme saline conditions under which Pi grows are a factor in production of the protective secondary metabolites in its natural desert habitat.

According to the above, under constant non-desert environmental conditions and constant water supply, the Pi infusion and Pi extracts are not expected to exhibit the same anti-oxidant activity as that of the wild type.

SUMMARY OF THE INVENTION

The present invention relates to an infusion prepared from Pi or to a composition comprising said infusion, for use in achieving anti-oxidant, protective and anti-neuroinflammatory effects in a patient in need thereof.

The present invention relates to the use of Pi infusion or to composition comprising the same for producing an anti-oxidant effect in living cell. More preferably, said living cells are brain cells. More preferably, said brain cells are neuronal brain cells. More preferably, said brain cells are astrocytes.

According to the present invention, Pi infusion is used to protect cells, more preferably brain astrocytes from $H_2O_2$-induced cell death.

According to the present invention, Pi infusion is used to protect cells from oxidizing species. More preferably, Pi infusion is used to protect astrocytes from oxidizing species. More preferably, Pi infusion is used to protect microglial cells from oxidizing species. More preferably, Pi infusion is used to treat conditions associated with the presence of species such as peroxynitrite (ONOO—), nitric oxide (NO.) and peroxyl radicals.

According to the present invention, Pi infusion is used to reduce the levels of intracellular ROS.

The present invention further relates to the use of Pi infusion in the preparation of a medicament for induction of GDNF in cells.

The present invention further relates to the use of Pi infusion in the preparation of a medicament to protect astrocytes from ischemia-induced cell death.

Thus the present invention further relates to the use of Pi infusion in the preparation of a medicament for inhibiting SAPK/JNK-activation.

The present invention further relates to the use of Pi infusion in the preparation of a medicament for attenuating glutamate secretion.

In the present invention, infusion prepared from Pi could downregulate NO production from LPS-activated microglial cells.

The present invention further relates to the use of Pi infusion in down-regulation of IL-6 secretion in microglial cells.

The present invention further relates to the use of Pi infusion in down-regulation of IL-1β secretion in microglial cells.

According to the present invention, not only the wild type Pi can protect astrocytes from H2O2-induced cell death, but also cultivated Pi.

According to the present invention, not only the wild type Pi can inhibit NO production from activated microglial eel is but also cultivated Pi.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

DETAILED DESCRIPTION OP THE INVENTION

The present invention relates to the use of Pi infusion or to composition comprising the same for producing an antioxidant effect in living cells. More preferably, said living cells are brain cells. More preferably, said brain cells are astrocytes. More preferably, said brain cells are neurons.

In this application, "Pi infusion" means infusion prepared from Pi according to the present invention.

"Extract" means ethanolic extract.

According to the present invention, there is the use of Pi infusion for counteracting oxidative damage in cells, preferably astrocytes and neurons.

In a further embodiment, there is the use of Pi infusion for counteracting NO levels in cells, preferably microglial cells.

According to the present invention, Pi infusion is used to protect cells, more preferably brain astrocytes from $H_2O_2$-induced cell death.

According to the present invention, Pi infusion is used to reduce the levels of intracellular ROS produced following treatment with $H_2O_2$, $ZnCl_2$, glutamate or ABAP. The beneficial effects of the Pi infusion are also demonstrated by the inhibition of NO levels secreted from LPS-activated microglial cells. Substances that can protect brain cells from oxidative stress are potential tools for the treatment of brain injuries and neurodegenerative diseases.

According to the present invention, Pi infusion is used to protect cells from Conditions associated with the presence of $H_2O_2$ above normal levels. More preferably, Pi infusion is used in the treatment of ischemia reperfusion. More preferably, Pi infusion is used to protect astrocytes from $H_2O_2$-induced cell death.

Figure 1:
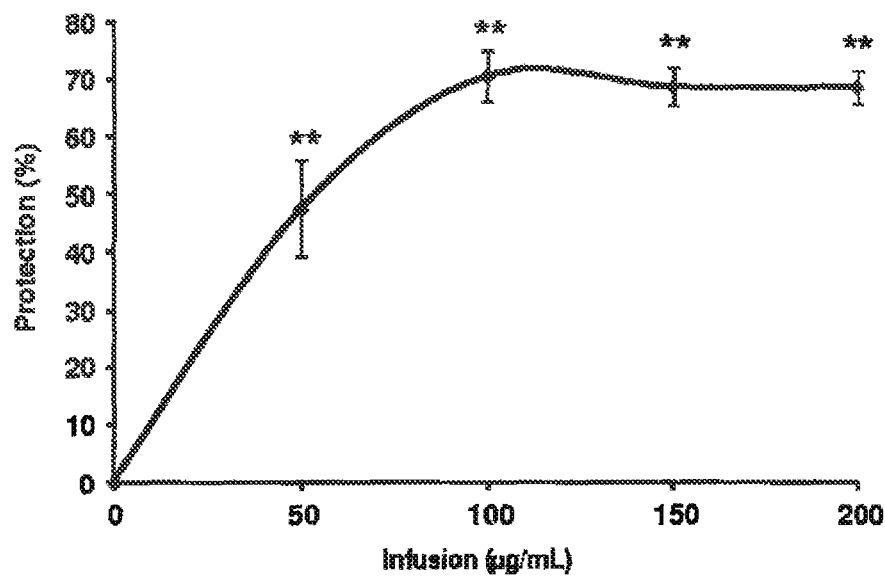
FIG. 1 shows that Pi infusion protects astrocytes from $H_2O_2$-induced cell death in a dose-dependent manner.

In the present invention, $H_2O_2$ exposure is used as a model of ischemia reperfusion. The concentration of $H_2O_2$ used in the working examples (175-200 µM) resembles the concentration reported in rat striatum under ischemic conditions. In order to characterize the ability of the Pi infusion to protect against $H_2O_2$-induced oxidative stress, inventors assessed changes in cell viability and intracellular ROS production, using a model in which oxidative stress was induced by the addition of $H_2O_2$ to cultures of primary astrocytes. Exposure of normal primary astrocytes to $H_2O_2$ resulted in the time and concentration-dependent death of astrocytes at 20 h after exposure (data not shown). To find out whether the Pi infusion has a protective effect and to determine the optimal concentration of the extract needed for such an effect, astrocytes were pre-incubated with different concentrations of Pi infusion. $H_2O_2$ was then added and was determined after 20 h. Results show that the Pi infusion exhibited a protective effect against $H_2O_2$-induced cell death in a dose-dependent manner (FIG. 1).

Figure 2:
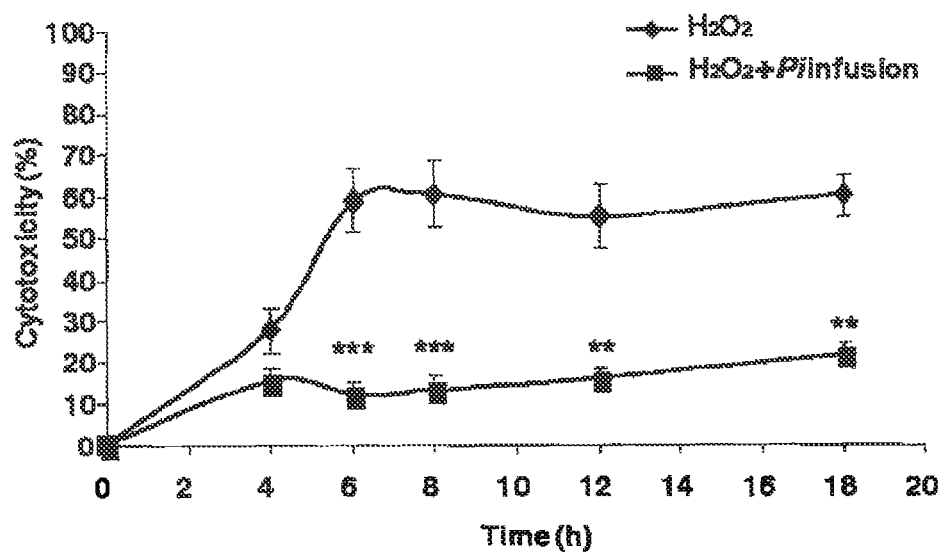
FIG. 2 shows time-course of the protective effect of the Pi infusion on astrocytes.

The kinetics of $H_2O_2$ cytotoxicity and inhibition in the presence of the Pi infusion are presented in FIG. 2. As shown in that figure, $H_2O_2$-induced cytotoxicity reached its maximal level 6 h after the application of $H_2O_2$. The Pi infusion prevented the increased incidence of cell death for at least 18 h—the latest time point examined.

Figure 3:
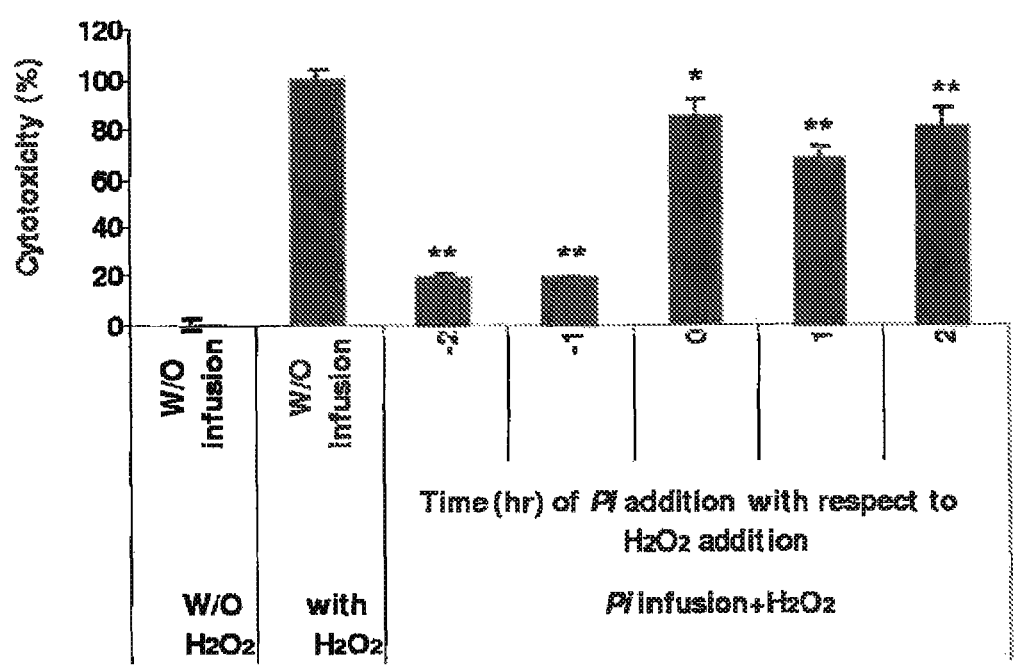
FIG. 3 shows that pre-incubation of astrocytes with Pi infusion is a prerequisite for the protective effect against $H_2O_2$ cytotoxicity.

To determine the optimal timing of the application of the Pi infusion to ameliorate the effect of $H_2O_2$, the cells were pre-incubated with Pi infusion for 2 h or 1 h, co-treated or post-treated with $H_2O_2$ (FIG. 3.).

In addition to $H_2O_2$, various other species, such as peroxynitrite ($ONOO^-$), nitric oxide ($NO^-$) and peroxyl radicals, have been found to oxidize DCFH to DCF in cell cultures.

According to the present invention, Pi infusion is used to protect cells from oxidizing species. More preferably, Pi infusion is used to protect astrocytes from oxidizing species. More preferably, Pi infusion is used to protect microglial cells from oxidizing species. More preferably, Pi infusion is used to protect neuronal cells from oxidizing species. More preferably, Pi infusion is used to treat conditions associated with the presence of species such as peroxynitrite ($ONOO^-$), nitric oxide ($NO^-$) and peroxyl radicals.

Cellular Antioxidant Activity of Pi Infusion.

Intracellular ROS production was detected using the non fluorescent cell permeating compound, 2'7'-dichlorofluorescein diacetate (DCF-DA). DCF-DA is hydrolyzed by intracellular esterases and then oxidized by ROS to a fluorescent compound 2'-7'-DCF. Peroxyl radicals are generated by thermolysis of 2,2'-Azobis(amidinopropane) (ABAP) at physiological temperature. ABAP decomposes at approximately $1.36 \times 10^{-6}$ $s^{-1}$ at 37° C., producing at most $1 \times 10^{12}$ radicals/ml/s.

Antioxidant Activity for Astrocytes: astrocytes were plated onto 24 wells plates (300,000 cells/well) and were incubated for 1 hr with Pi infusion. Then astrocytes were preloaded with DCF-DA for 30 min, washed, and ABAP (0.6 mM final concentration) was then added.

Antioxidant Activity for Microglial Cells: microglial cells were plated in DMEM containing 2% FBS, 2 mM glutamine, 100 U/mL penicillin and 100 µg/mL streptomycin, onto 24 wells plates (150,000 cells/well) and were incubated for 1 hr with Pi infusion. Then microglial cells were preloaded with DCF-DA for 30 mM, washed twice with PBS, and ABAP (0.6 mM final concentration) was then added.

The fluorescence, which indicates ROS levels, was measured in a plate reader with excitation at 485 nm and emission at 520 nm.

It is shown in the present invention that Pi infusion reduced 2,2'-azobis(amidinopropane) (ABAP)-mediated peroxyl radicals levels in astrocytes and microglial cells.

Figure 7A:
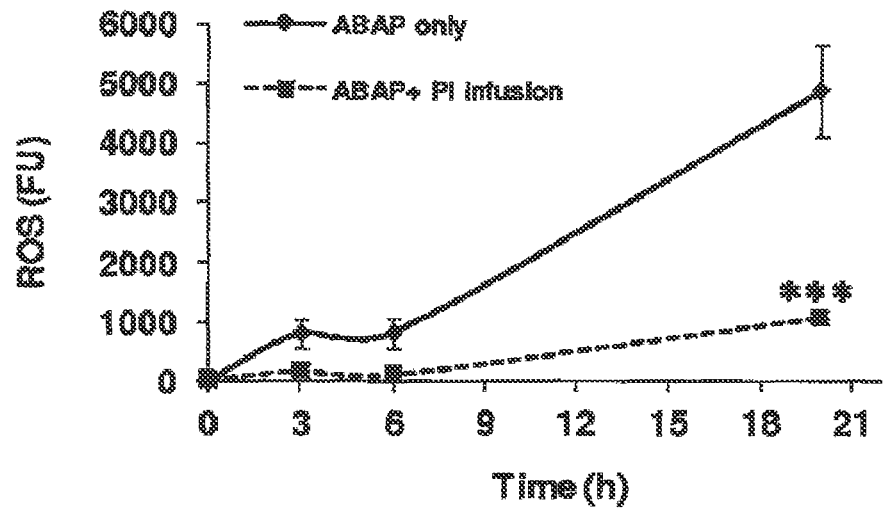
FIG. 7 shows peroxyl radical-induced oxidation of DCFH to DCF in primary astrocytes and the inhibition of oxidation by the Pi infusion.
Figure 7B:
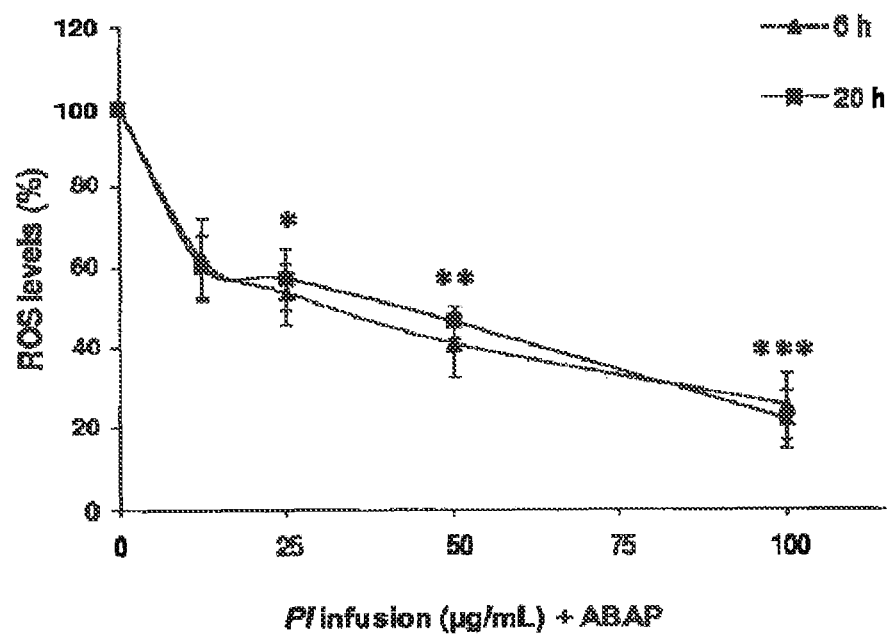

Inventors have used a cellular antioxidant activity assay to measure the ability of compounds present in the Pi infusion to enter the cells and prevent the formation of DCF by ABAP-generated peroxyl radicals. The kinetics of DCFH oxidation in astrocytes by peroxyl radicals generated from ABAP is shown in FIG. 7A. As shown in that figure, ABAP generates radicals in a time-dependent manner and the treatment of cells with the Pi infusion moderated this induction. The increase in ROS-induced fluorescence was inhibited by the Pi infusion in a dose-dependent manner, as shown in FIG. 7B. This indicates that compounds present in the Pi infusion entered the cells and acted as efficient intracellular hydroperoxyl radical scavengers.

According to the present invention, Pi infusion is used to reduce the levels of intracellular ROS. For example, it may be shown that PI infusion inhibits the $H_2O_2$- and $ZnCl_2$-induced generation of ROS.

Figure 4A:
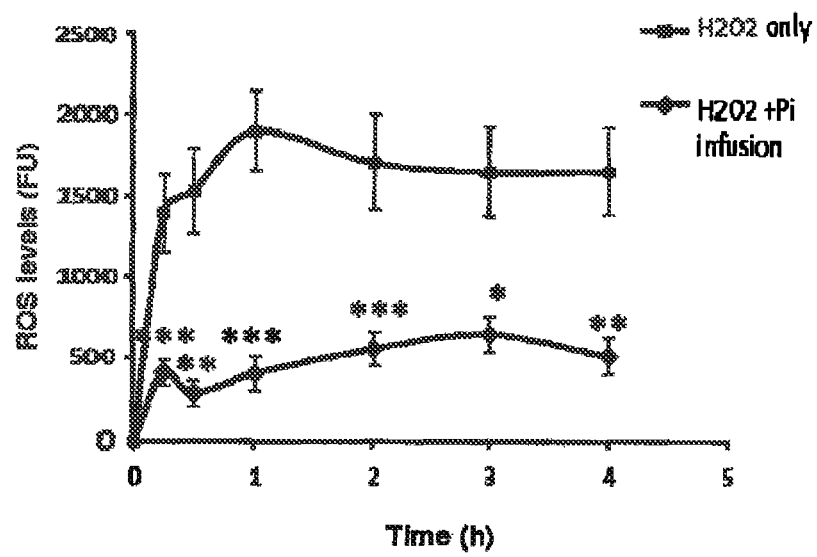
FIG. 4 shows that Pi infusion attenuates $H_2O_2$-induced ROS production in astrocytes.
Figure 4B:
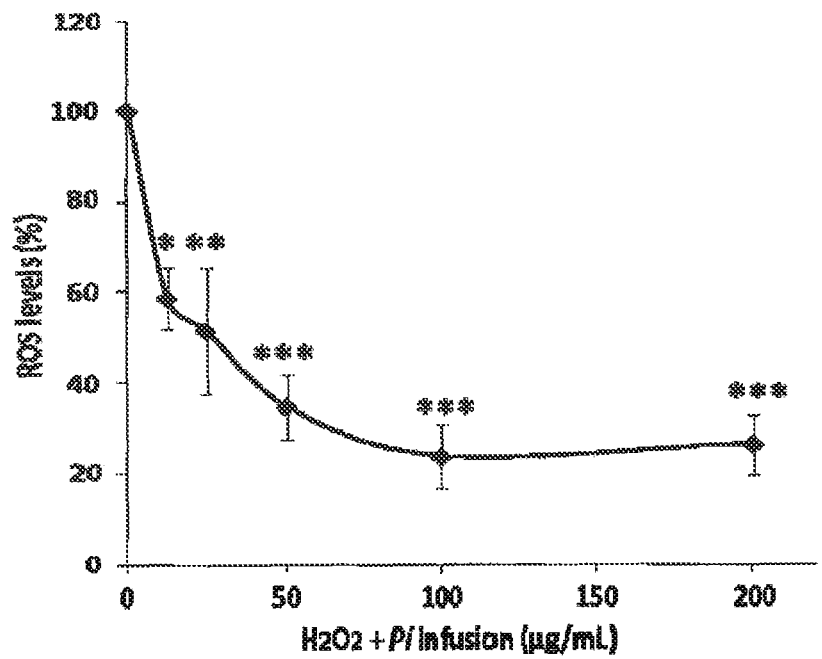
Figure 5:
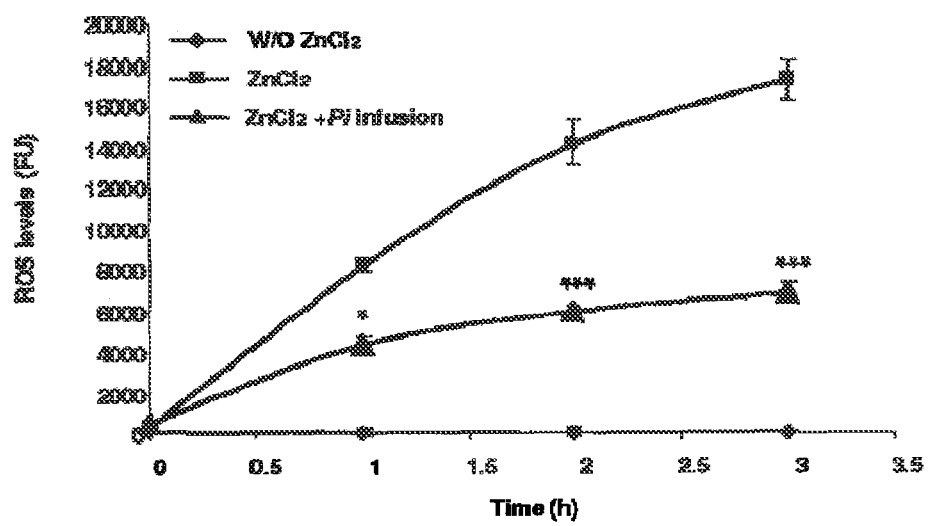
FIG. 5 shows that Zinc induces ROS generation and the Pi infusion attenuates ROS production following treatment of astrocytes with zinc.

$H_2O_2$-induced cell death is accompanied by an increase in ROS levels. In order to determine whether our Pi infusion could inhibit the production of ROS that is induced by $H_2O_2$, inventors assessed the intracellular generation of ROS and tested whether treatment of astrocytes with the pi infusion affected intracellular ROS levels. For the study of the preventive effects against intracellular ROS formation, the cells were pre-loaded with the ROS indicator DCF-DA and were treated with various concentrations of Pi infusion before the application of $H_2O_2$. ROS formation was determined by examining fluorescence every hour for 4 h. As shown in FIG. 4A, $H_2O_2$ induced the production of ROS in astrocytes, with the maximum levels of ROS produced after 1 h. Pre-treatment of astrocytes with the Pi infusion inhibited the $H_2O_2$-induced elevation of the levels of intracellular ROS in a dose-dependent manner (FIG. 4B). Inventors also found that treatment with $ZnCl_2$ increased ROS generation in astrocytes and that, similar to the effect of the Pi infusion on $H_2O_2$-induced generation of ROS, this infusion greatly attenuated $ZnCl_2$-induced ROS generation (FIG. 5).

Figure 6:
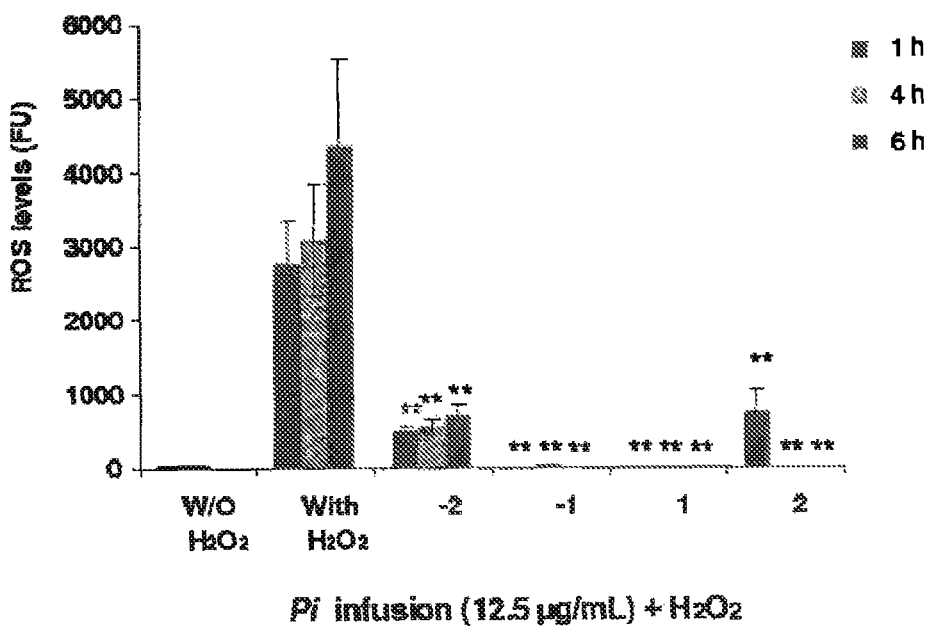
FIG. 6 shows that Pi infusion is similarly effective in attenuating ROS production when applied before or after $H_2O_2$.

To determine the time at which the Pi infusion best ameliorates $H_2O_2$-induced ROS production, the cells were pre-incubated with Pi infusion for 2 h or 1 h, co-treated or post-treated (for 2 h or 1 h) with $H_2O_2$. Interestingly, in contrast to the results obtained in our cell protection assay (FIG. 3), the Pi infusion was similarly effective in attenuating ROS production when it was pre-incubated with the cells and when it was applied after the $H_2O_2$ (FIG. 6). This may indicate that Pi treatment sets the cells into a defensive state that helps them to contend with oxidative stress and that it takes about 1 h to get the cells into that defensive state. If this is the case, it indicates that the Pi infusion is not only an anti-oxidant cocktail, but also contains compounds that might bind to a cell surface or intracellular receptor/s to conduct a protective signal.

The present invention further relates to the use of Pi infusion in the preparation of a medicament for scavenging free-radical activity.

Figure 8:
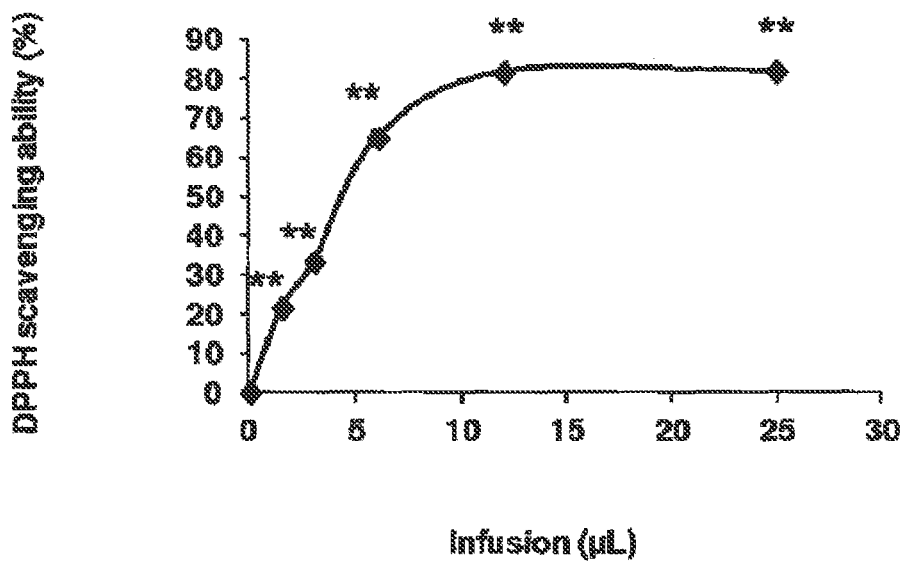
FIG. 8 shows DPPH radical scavenging activity of the Pi infusion.
Figure 19:
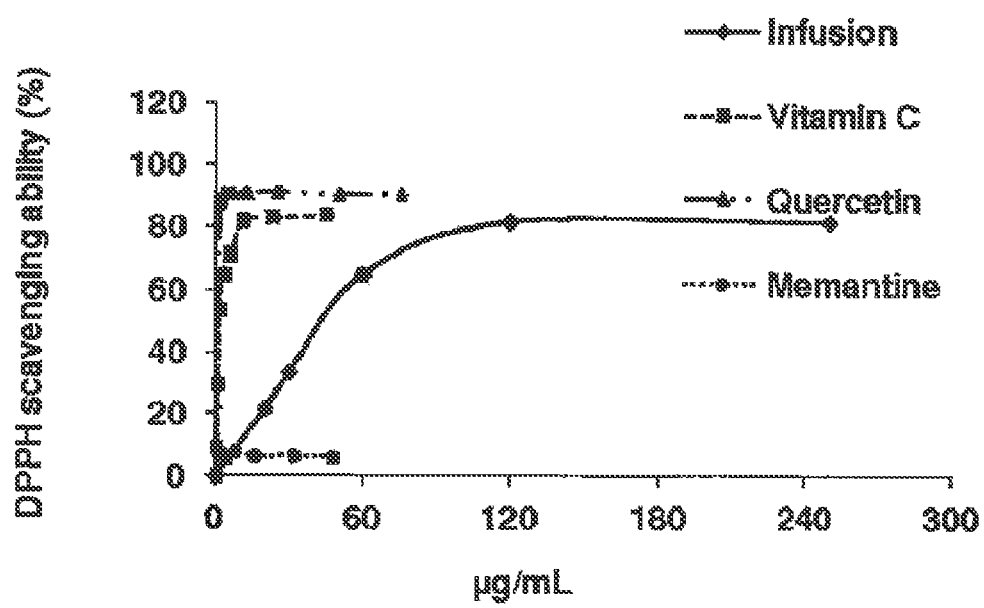
FIG. 19 shows DPPH radical scavenging activity of Pi infusion compared to memantine, quercetin and vitamin C.

Since many low-molecular-weight antioxidants may contribute to cellular antioxidant defense properties, inventors analyzed radical scavenging activity rather than seeking specific antioxidants. Pi infusion was found to be a very potent free-radical scavenger with an $IC_{50}$ value of 45 µg/mL and 80% inhibition of DPPH absorbance at 517 nm (FIGS. 8 and 19).

The present invention further relates to the use of Pi infusion in the preparation of a medicament for induction of GDNF in cells.

The present invention further relates to the use of Pi infusion in the preparation of a medicament to protect astrocytes from ischemia-induced apoptosis.

According to the present invention, Pi infusion stimulates GDNF transcription in astrocytes.

Figure 9:
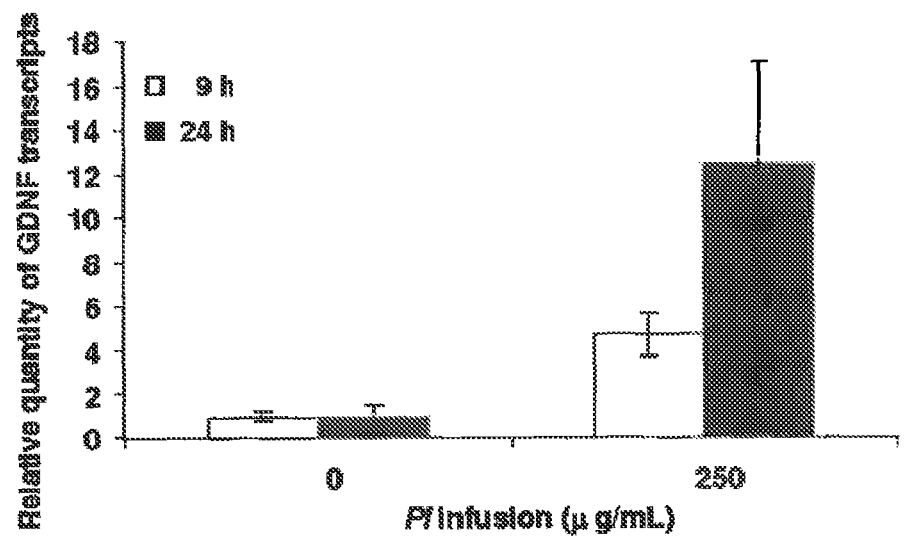
FIG. 9 shows that treatment with the Pi infusion increases the levels of GDNF transcript in primary astrocytes.

The contrast between the need for a pre-incubation of the cells with the infusion (FIG. 3) in order to gain the protective effect and the fact that the timing of the addition of the Pi infusion did not appear to affect the ability of the treatment to neutralize ROS levels (FIG. 6) led the inventors to examine whether another factor aside from antioxidant activity might be involved in the beneficial effect of the Pi infusion. One possible factor could be GDNF secretion. It has been previously shown that GDNF protects astrocytes from ischemia-induced apoptosis. Thus, inventors raised the possibility that the protective effect of Pi infusion on astrocytes suffering oxidative stress might be at least partially due to the induction of GDNF by the Pi infusion. This possibility might be supported by the need for pre-incubation of the Pi infusion with the cells in order to elicit the protective effect against $H_2O_2$-induced cell death. To test this possibility, inventors used real-time PCR and quantified GDNF mRNA. Primary astrocytes were treated with different concentrations of Pi infusion for several incubation periods and levels of GDNF transcripts were determined. The results of this work showed that incubation with Pi infusion at an optimal concentration of 250 µg/mL leads to a 5-fold increase in GDNF mRNA levels following 9 h of incubation and a 10-fold increase in GDNF mRNA levels following 24 h of incubation (FIG. 9).

Figure 20A:
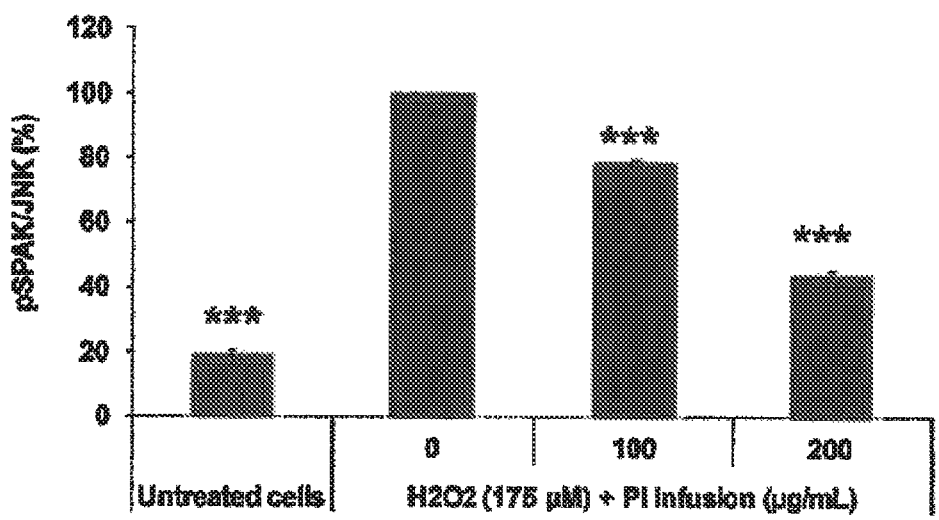
FIGS. 20(A and B) show that Pi infusion suppresses $H_2O_2$-induced SAPK/JNK phosphorylation in astrocytes, without affecting the total amount of SAPK/JNK.
Figure 20B:
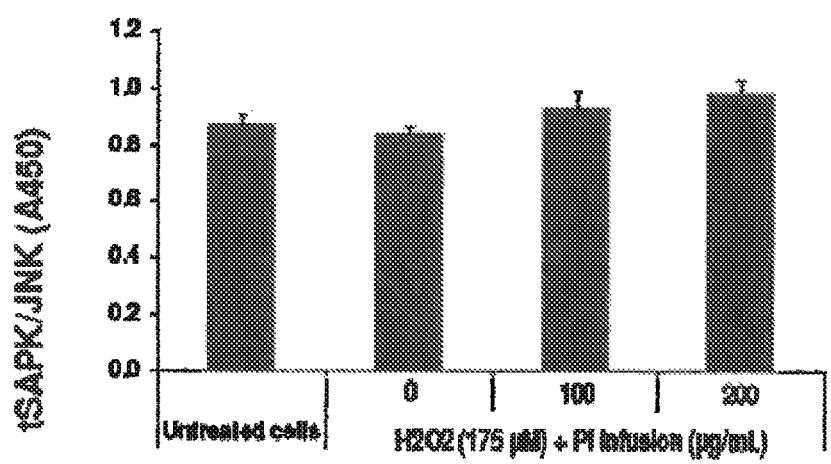
Figure 21:
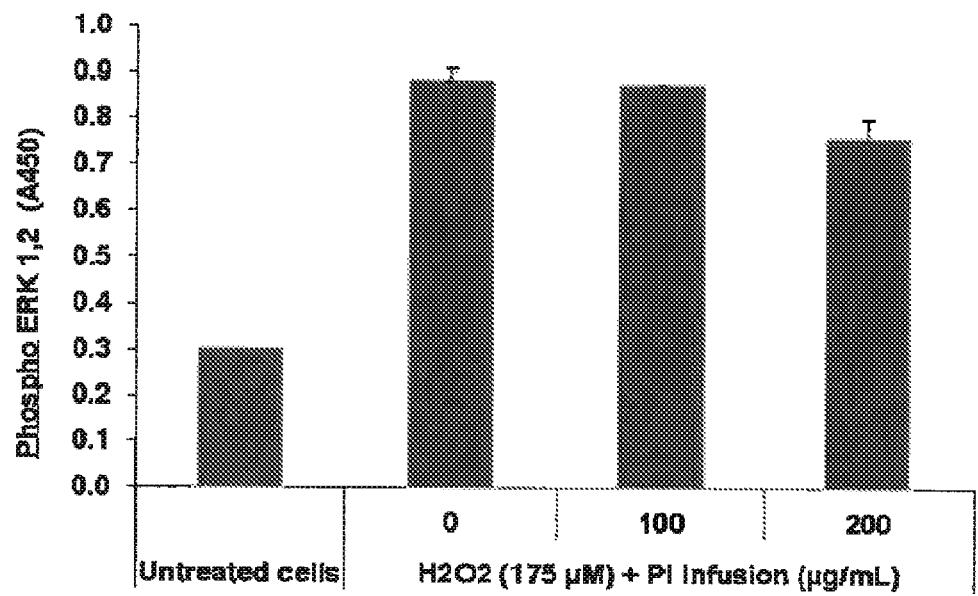
FIG. 21 shows the effect of Pi infusion on $H_2O_2$-induced phosphorylation of ERK 1/2 in astrocytes.

The mitogen-activated protein kinases (MAPKs) are a family of secondary messengers that convey signals from the cell surface to the nucleus in response to a wide range of stimuli, including stress. Stress-activated protein kinases (SAPK)/Jun amino-terminal kinases (JNK) and extracellular regulated kinase (ERK) are members of the MAPK family. Inventors attempted to determine whether the protective effect of Pi infusion against $H_2O_2$-induced cell death is mediated through the inhibition of $H_2O_2$-induced SAPK/JNK and/or ERK phosphorylation. As can be seen in FIGS. 20A and 20B and 21, Hydrogen peroxide provoked phosphorylation of extracellular regulated kinase (ERK) and Stress-activated protein kinases (SAPK)/c-Jun NH(2)-terminal kinase (JNK). Pi infusion inhibited 70% of the $H_2O_2$-induced phosphorylation of SAPK/JNK in astrocytes, without affecting the total amount of SAPK/JNK in the cells. Pi infusion also inhibited but with much smaller amount of the $H_2O_2$-induced phosphorylation of ERK 1/2. Thus, inventors suggest that the protective effects of Pi infusion on brain astrocytes under oxidative stress might be partially attributed to the inhibition of SAPK/JNK phosphorylation.

Thus the present invention further relates to the use of Pi infusion in the preparation of a medicament for inhibiting SAPK/JNK-activation. More preferably, the present invention further relates to the use of Pi in the preparation of a medicament for $H_2O_2$-induced phosphorylation of SAPK/JNK in astrocytes.

When activated by pro-inflammatory stimuli, microglial cells secrete substantial levels of glutamate. The consequences could range from interference with normal neurotransmission to excitotoxicity for neurons in the vicinity. Treatment of microglial cells with LPS is known to increase the accumulation of glutamate in the culture medium. To test whether Pi infusion affects the release of glutamate from microglial cells, LPS was added to the culture media of the cells in the presence or absence of pi infusion. Stimulation of the cells with LPS resulted in a 2.6 fold increase in glutamate secretion, and Pi infusion inhibited 77% of the induced levels of glutamate (see FIG. 25).

The present invention further relates to the use of Pi infusion in the preparation of a medicament for attenuating glutamate secretion. More preferably, the present invention relates to the use of Pi infusion in the preparation of a medicament for attenuating glutamate secretion in LPS-stimulated microglial cells.

It has been surprisingly found that not only the wild type Pi can protect astrocytes from $H_2O_2$-induced cell death, but also cultivated Pi.

It has been surprisingly found that not only the wild type Pi can inhibit NO production from activated microglial cells but also cultivated Pi.

Figure 16:
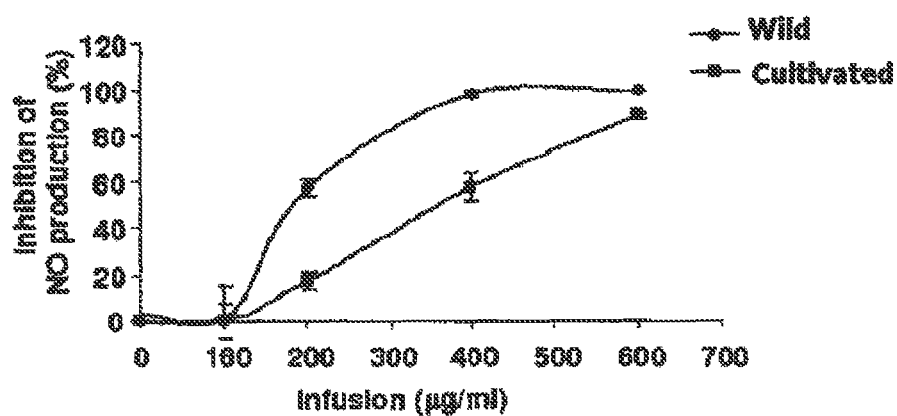
FIG. 16 shows inhibition of NO production by activated microglial cells in response to Pi infusion—a comparison between the wild and the cultivated plant.

In order to find out whether the cultivated plant has similar capabilities, and could serve as a more available source of the active phytochemicals inventors have compared the abilities of the infusion prepared of cultivated and wild type Pi to inhibit NO production from activated microglial cells. FIG. 16 shows that the cultivated plant exhibits inhibitory activity although to a lower extent compared to the wild Pi.

Figure 17:
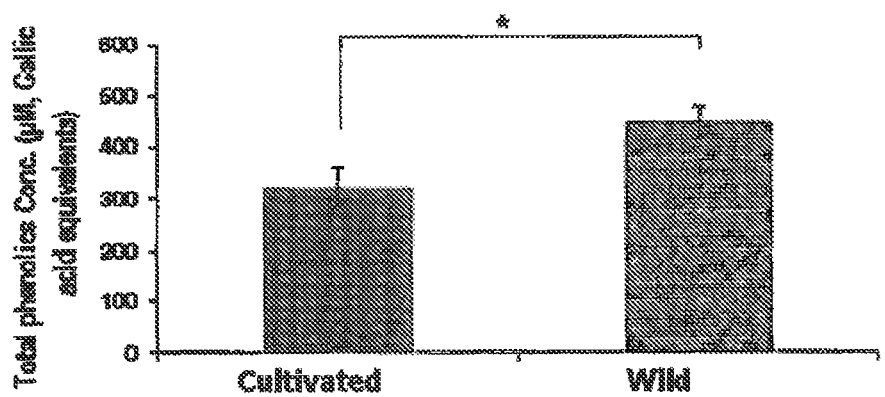
FIG. 17 shows that Pi infusion is enriched with total phenolics.

As evidence, it is shown that Pi infusion prepared from wild type and cultivated Pi contains large amount of total phenolics. The levels of total phenolics in infusion prepared from wild type Pi and cultivated Pi were determined using the Folin-Ciocalteu reagent. FIG. 17 shows that both preparations contain large amounts of total phenolics, although the wild type Pi contains larger amounts when compared to the cultivated Pi.

It has been noted that it is almost impossible commercialize the Pi or the Pi infusion by collecting the plant from its natural habitat. For commercialization purposes, plants should be grown in large masses under constant conditions so they could serve as a more available source of the active phytochemicals.

A significant influence of the irrigation regime on essential oil composition was found in experiments on *Pelargonium graveolens*: decreasing the amount of water to the point of creating water stress in the plant, changed the yield and composition of its oil: the water stressed plants gave a smaller biomass yield but the oil quality was higher, i.e., the citronellol/geraniol ratio was higher (Putievsky et al., *Flavor and Fragrance Journal* 5:121-123, 1990).

Sweet basil (*Ocimurn basilicum*) responded to mild or moderate water stress by increasing the essential oil content by 87 or 100%, respectively (Simon et al., *Journal of Essential Oil Research*, Volume 4, issue 1, 1992). Hydroponically grown *Mentha piperita* plants responded to an increase in osmotic stress, from −0.05 (control) to −0.6 MPa, by increasing both the content of the essential oil—from 44 to 71 µl/g dry weight—and the relative proportion of the sesquiterpenes in the oil (Charles et al., *Phytochemistry* 29:2837-2840, 1990).

According to the present invention, Pi plants that were given water supply greater than that of the natural desert habitat, exhibit similar biological activity as the wild plant.

In the present invention, "winter" is the period between November and February. Pi's natural habitat is the desert where which it is naturally irrigated only in the winter with an average precipitation amount of 20 mm.

"Cultivated Plants" means plants that were grown in the field were irrigated by the method of drip irrigation with 2 and 10 cubic meter of water per day in the winter (0-12° C.) and in the summer (20-35° C.), respectively. "Field" means an area of land enclosed and used for agricultural purposes.

"Wild Plants" means plants that were naturally grown in the desert and that were not irrigated by human.

Seeds were collected from a plant in the Negev desert were germinated in small pots and then transferred to the field. The salinity of the water used for irrigation is 350-600 ppm.

Figure 10A:
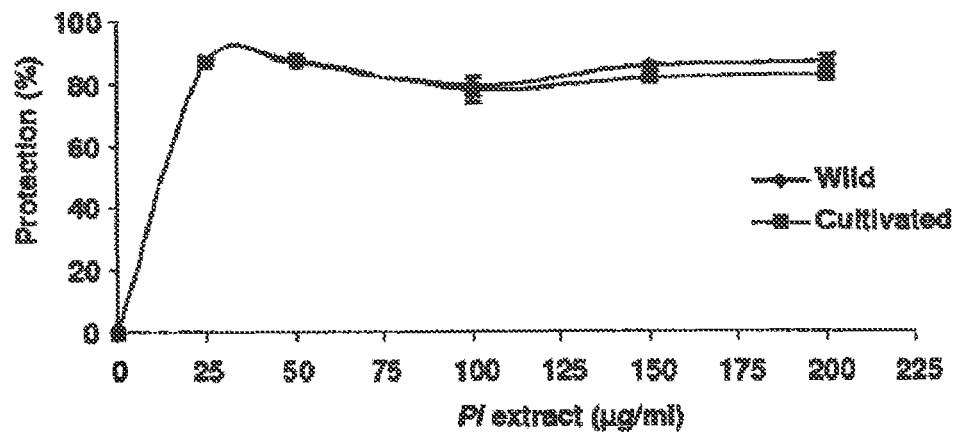
FIG. 10 shows that different extracts of Pi protect astrocytes from $H_2O_2$-induced cell death—a comparison between the infusion and the ethanolic extracts prepared from the wild or the cultivated plant.
Figure 10B:
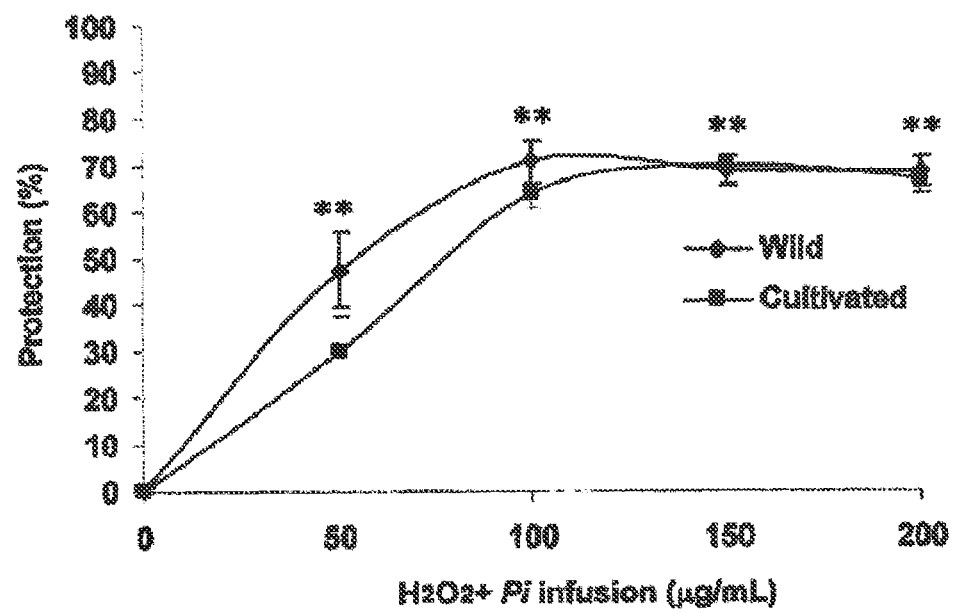

In order to find out whether the cultivated plant has similar capabilities, and could serve as a more available source of the active phytochemicals inventors have compared the efficiencies of ethanolic extracts and infusion's prepared of cultivated and wild type Pi to protect astrocytes from oxidative stress. For that purpose, astrocytes were treated (before stress induction) with different amounts of either the ethanolic extract (A) or infusion (B) prepared of Pi. FIG. 10A shows that there is no difference in the efficiencies of the different ethanolic extracts. FIG. 10B shows that at low concentrations, up to 100 ug/ml, the infusion prepared from wild type Pi is more efficient, however, at higher concentrations no differences were observed.

Thus, according to the present invention, it is provided Pi grown under the conditions selected from: irrigation 2 m$^3$/day, 0-12° C. and irrigation 10 m$^3$/day, 20-35° C. for use as anti-oxidant. In another embodiment, the present invention relates to the use of Pi grown under the conditions selected from: irrigation 2 m$^3$/day, 0-12° C. and irrigation 10 m$^3$/day, 20-35° C. in the preparation of an anti-oxidant.

It is known that treatment of neuronal cells with glutamate causes cell death. According to the present invention there is provided the use of Pi infusion in the preparation of a medicament for preventing glutamate-induced neuronal cell death.

Figure 18:
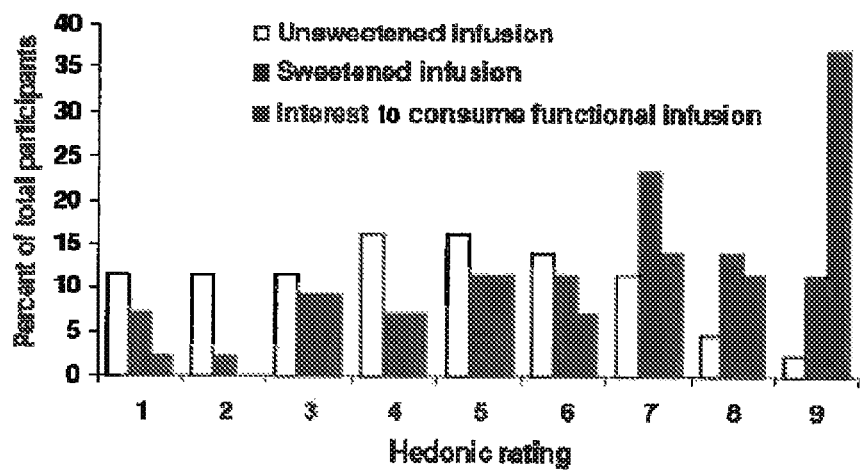
FIG. 18 shows the results of sensory evaluation of infusion prepared from wild Pi.

FIG. 18 shows the extent of satisfaction from the taste of the infusion, and the extent of motivation of 43 non-trained people to consume an infusion with such a taste that has anti-neurodegenerative properties.

Effect of Seasons on the Activity of the Protective Compounds.

Figure 11A:
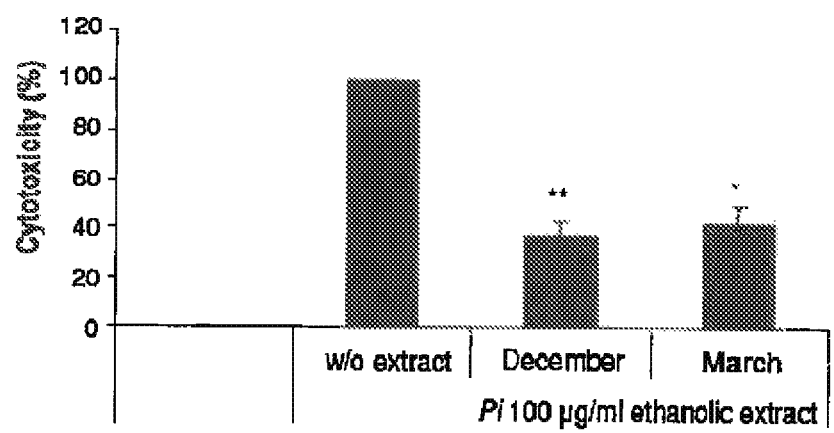
FIG. 11 shows that different extracts of Pi protect astrocytes from $H_2O_2$-induced cell death—a comparison between extracts prepared from plants that were harvested at different periods of the year.
Figure 11B:
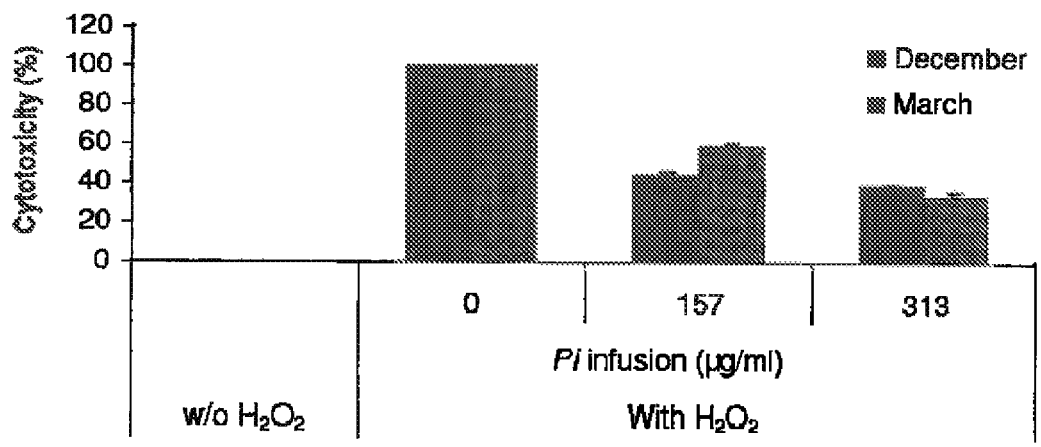

In order to test if the extent of the protective ability is changing in different seasons, Pi was collected at different time point of the year (March and December) and was extracted either by ethanol (FIG. 11A) or by the procedure for infusion preparation (FIG. 11B). Astrocytes were preincubated for 2 hr with these extracts. FIG. 11A: 100 µg/ml ethanolic extract; FIG. 11B: the indicated amounts of infusion. H2O2 was then added, and the cytotoxicity was measured 20 hr later. FIGS. 10-12 and 14 show that both ethanolic extract and infusion prepared from Pi contain compounds that can protect astrocytes from oxidative stress.

The Protective Compounds are present in Infusions Prepared from the Stems, Leaves and Flowers of Pi.

Figure 12:
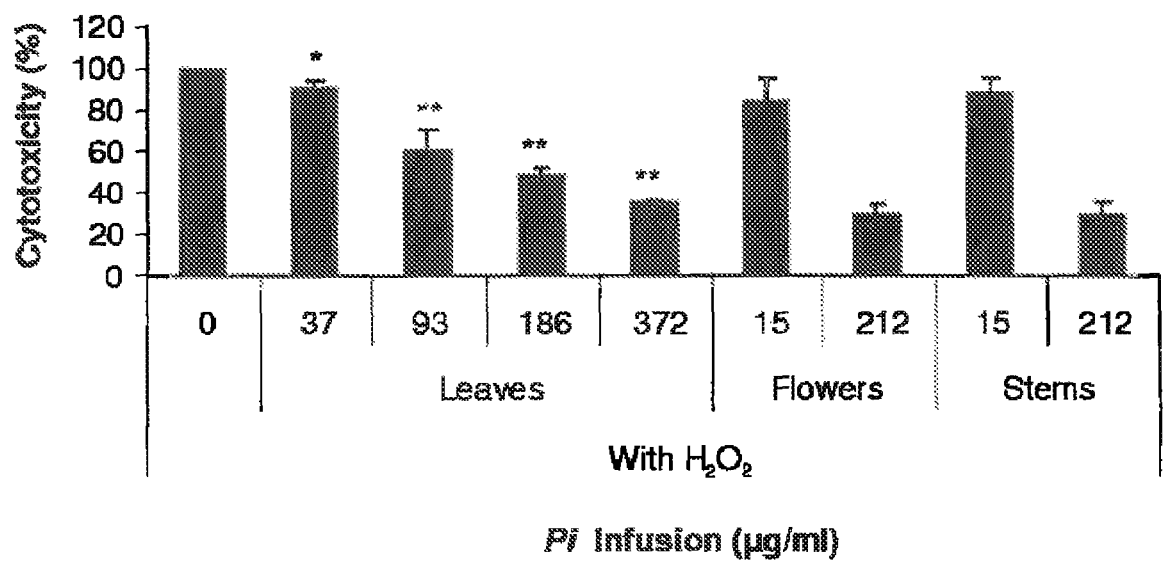
FIG. 12 shows that infusions prepared from each of the aerial parts of Pi contain the protective activity.

According to FIG. 12, the protective compound's of Pi can be found in an infusion prepared from the stems, leaves and flowers and the effect is concentration dependent. Astrocytes were preincubated for 2 hr with, infusion prepared from different parts of Pi. H2O2 were then added and the cytotoxicity was measured 20 hr later by LDH *p<0.05, **p<0.01.

LPS Induces NO Production by Microglial

Figure 13:
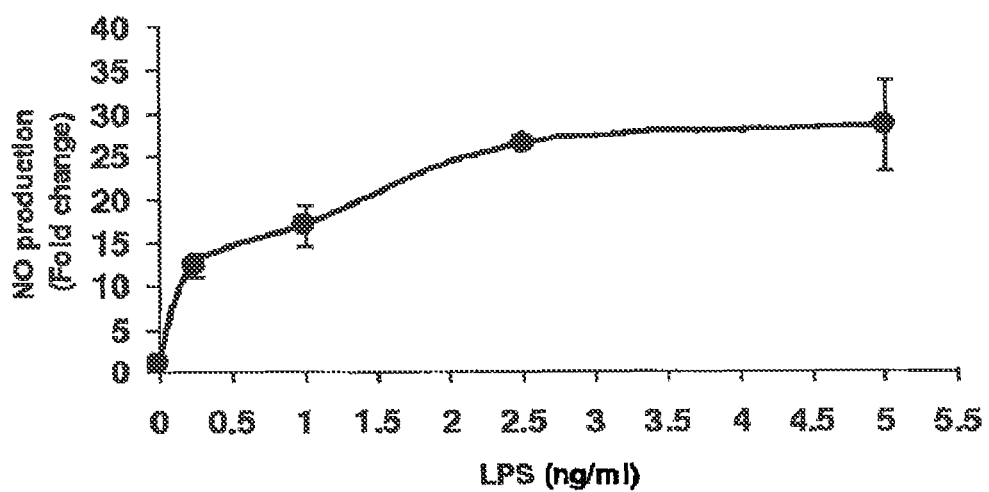
FIG. 13 shows that LPS induces NO production from microglial cells.

FIG. 13 shows NO production from primary microglia cells that were treated with different concentrations of LPS (lipopolysacharride). Increasing the concentration of the inflammation elicitor LPS results in increased NO production. *Pulicaria incisa* (Pi) was extracted by ethanol, lyophilized and re-suspended in DMSO. Microglial cells were seeded (70,000 cells per well in a 24 well plate) and the day after were treated with LPS for 20 hrs. NO concentrations in the media were determined by Griess reagent.

In another embodiment, the present invention relates to the use of an infusion prepared from Pi in the preparation of a medicament for downregulating NO production from cells, more preferably, from microglial cells.

Figure 14:
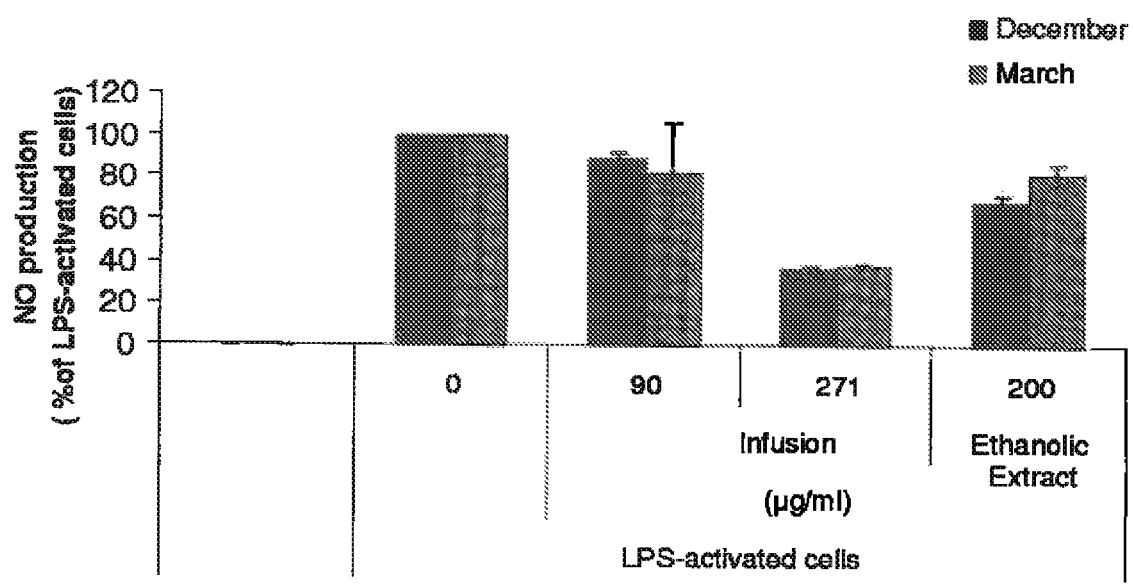
FIG. 14 shows that Pi extracts downregulate NO production from LPS-activated microglial cells—a comparison between different periods of harvest.

In the present invention, infusion prepared from Pi could downregulate NO production from LPS-activated microglial cells. Inventors have also tested whether the extent of the inhibitory activity is changing at different seasons. Thus, infusion was prepared from Pi that was collected either in March or in December and its effect on NO production was tested. FIG. 14 shows that Pi collected in both seasons contain inhibitory compound that could dowuregulate NO production in a concentration dependent manner. The kinetics of NO production and the inhibitory effect of Pi infusion are demonstrated in FIG. 15.

As to FIG. 14, an infusion and an ethanolic extract were prepared from Pi that was collected either in March or in December. Microglial cells were treated with different amounts of these infusions and ethanolic extracts and were activated by LPS. NO was determined using Griess reagent 20-24 hr later.

In a still another embodiment, the present invention relates to the use of Pi infusion in the preparation of a medicament for down-regulation of glutamate secretion from cells, more preferably from activated microglial cells.

In order to implement the present invention, the following materials were used: LPS (*E. coli* 0127 B:8) and 2-mercaptoethanol were purchased from Sigma Chemical Co. (St Louis, Mo., USA); RPMI 1640 was obtained from Gibco BRL (Gaithersburg, Md., USA); Dulbecco's Modified Eagle's Medium (DMEM), Leibovitz-15 medium, glutamine, antibiotics (10,000 IU/ml penicillin and 10,000 μg/ml streptomycin), soybean trypsin inhibitor and fetal bovine serum (FES) were purchased from Biological Industries (Beit Haemek, Israel); Dimethyl sulphoxide (DMSO) was obtained from Applichern (Darmstadt, Germany); Griess reagent was obtained from Cayman chemical, Mich., USA.

Preparation of Pi infusion according to the present invention is as follows: Plants used for wild Pi experiments were collected in Nekarot Wadi in the Arava Valley on April, 2005, and the plant's voucher specimen (M86) has been kept and authenticated as part of the Arava Rift Valley Plant Collection; VPC (Dead Sea ft Arava Science Center, Central Arava Branch, Israel, http://www.deadseaarava-rd.co.jl/_Uploads/dbsAttachedFiles/Arava_Rift_Valley_Plant_Collection.xls) under the accession code AVPC0193. Freshly collected plants (aerial parts only) were dried in 40° C. for three days. Preparation of Pi infusion was initiated by soaking a 15 mL tube containing dried Pi (1 gr/10 mL) in a beaker containing 200 mL boiling DDW. The beaker was allowed to cool at RT for 30 min. The tube was centrifugation (4000 RPM, 10 min, RT), the supernatant was collected, filtered, and aliquots were stored at −20° C. until use. In order to determine the extract concentration; a sample of the filtered supernatant was lyophilized to obtain extract powder. The averaged concentration of the various preparations that were tested was 10 mg/mL.

The present application shows (FIG. 17) that Pi infusion is enriched with total phenolics. The concentration of total phenolics in an infusion prepared from wild type or cultivated Pi was determined using the Folin-Ciocalteu reagent. *$p<0.05$.

The present application shows (FIG. 18) the results of sensory evaluation of infusion prepared from wild Pi. Forty three none trained persons were participated in the sensory evaluation of Pi infusion. They were asked to rate (i) how much they liked the taste of infusion using a 9-point hedonic scale (1=dislike extremely and 9=like extremely), and (ii) the extent of interest to consume this infusion if found as a functional infusion for prevention/treatment of neurodegenerative diseases.

Nitrite Quantification.

For NO measurements, $1 \times 10^5$ cells/well were plated in a 24-well tissue culture plate. After 36 h of incubation in RPMI-1640 (without phenol red), containing 2% FBS, 2 mM glutamine, 100 U/ml penicillin, 100 μg/ml streptomycin, 1 mM sodium pyruvate, and 50 μM β-mercaptoethanol, cells were stimulated with LPS (4.5 ng/ml). Nitrite accumulation, an indicator of NO release, was measured in the culture medium with Griess reagent 20 h after an LPS challenge. Briefly, 100 μl of cell culture medium were incubated with Griess reagent at room temperature for 10 min, and the absorbance was then read at 550 nm in a microplate reader. Fresh culture medium was used as the blank in all the experiments.

Determination of Cell Viability.

Cell viability was determined using two methods: 1. a modification of the crystal violet cell staining (Kueng et al., 1989). 2. LDH activity. Cell viability was determined using a commercial colorimetric assay (Roche Applied Science, Germany) measuring lactate dehydrogenase (LDH) activity released from the cytosol of damaged cells into the incubation medium.

Measurement of IL-1β, IL-6 and Glutamate Levels in Conditioned Media.

For cytokine and glutamate measurements, $3.5 \times 10^4$ cells/well were plated on a 24-well tissue culture plate. After 24 h of incubation in DMEM containing 10% FES, cells were stimulated with LPS (100 ng/mL) and treated with different concentrations of Pi infusion. Conditioned media were collected twenty four hours later, and were tested for rat IL1β levels with a rat IL1β ELISA kit (Novas Biologicals; CO, USA), for rat IL-6 with Legend Max ELISA kit (BioLegend Inc. CA, USA) and for glutamate levels using a calorimetric enzymatic assay kit (glutamate assay kit, BioVision, CA, USA). All kits were used according to the manufacturer's instructions.

General Enabling Procedures

Determination of Anti-Oxidant Activity of Pi Infusion.

In order to determine whether a Pi infusion or composition comprising the same gains an anti-oxidant activity in $H_2O_2$-treated cultured astrocytes, a person skilled in the art may take the following steps:

1. Produce a primary culture of rat brain glial cells according to the method described in "Protective effects of the essential oil of *Salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
2. Separate astrocytes from other cell types in the culture according to the method described in "Protective effects of the essential oil of *Salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
3. Plate astrocytes (300,000 cells/0.5 ml/well of 24 wells plate) and incubate (37° C., 5% CO2) for 24 hr as described in: Elmann, A., Telerman, A., Mordechay, S., Erlank, Rindner, M., Ofir, R. and Beit-Yannai, E. (2011). Extract of *Achillea fragrantissima* downregulates ROS production and protects astrocytes from oxidative-stress-induced cell death. In: "Neurodegenerative Diseases—Processes, Prevention, Protection and Monitoring", ISBN 978-953-307-485-6, (Raymond Chuen-Chung Chang, ed). InTech Publisher. http://www.intechopen.corn/articles/show/title/extract-of-aehillea-fragrantissima-down-regulates-ros-production-and-protects-astrocytes-from-oxidati;
4. Replace growth medium with a fresh one containing 20 micromolars 2'7'-dichlorofluorescein diacetate (DCF-DA);
5. Incubate 30 min (37° C., 5% CO2);
6. Wash twice with PBS;
7. Replace with fresh medium;
8. Read fluorescence of "time 0" at 485 nm (Extinction) and 528 nm (Emmision).
9. Incubate the cultured cells for 2 hours with freshly diluted compound of the invention;
10. Add freshly diluted H2O2 (375 micromolars);
11. Read fluorescence at 1, 2, 3, 4 hr after the addition of $H_2O_2$ (Ex: 485 nm and Em: 528 nm).

Determination of Protective Activity of Pi Infusion.

In order to determine whether a Pi infusion or composition comprising the same gains a protective activity against $H_2O_2$-induced cell death in cultured astrocytes, a person skilled in the art should follow the following steps:

1. Produce a primary culture of rat brain glial cells according to the method described in "Protective effects of the essential oil of *Salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
2. Separate astrocytes from other cell types in the culture according to the method described in "Protective effects of the essential oil of *Salvia fruticosa* and its constituents on astrocytic susceptibility to hydrogen peroxide-induced cell death". 2009. A. Elmatm, S. Mordechay, M. Rindner, O. Larkov, M. Elkabetz, U. Ravid. Journal of agricultural and food chemistry. 57(15):6636-41;
3. Incubate the cultured astrocytes (37° C., 5% CO2) for 2 hours with freshly diluted composition of the invention;
4. Add 175-200 micromolars of freshly diluted H2O2;
5. Incubate the culture for 20-24 hr (37° C., 5% CO2);
6. Measure cell cytotoxicity and viability by the colorimetric lactate dehydrogenase (LDH) assay (Roche Applied science) according to the manufacturer's instructions, and the crystal violet cell staining as follows:
7. Gently draw out medium from plate;
8. Transfer plate to a chemical hood;
9. Dispense 150 µl 5% formaldehyde (in PBS) to each well and incubate 15 min at RT;
10. Pour out formaldehyde to chemical waste and gently rinse under running tap water;
11. Remove excess water by tapping plate on a tissue paper;
12. Dispense 150 µl crystal violet solution (10 gr/liter, in water) to each well;
13. Incubate 15 min at RT (in the chemical hood);
14. Pour out crystal violet to chemical waste and gently rinse under running tap water until all residual dye is removed;
15. Tap plate on a tissue paper to remove remaining water;
16. Dispense 150 µl 33% aqueous glacial acetic acid to each well;
17. Measure absorbance using a microplate reader at 540 nm with 690 nm reference filter;
18. A reduction of at least 70% of cytotoxicity levels are indication for a protective activity in this assay.

Determination of Anti-Oxidant Activity Against the Peroxyl Radical Generating Molecule ASAP.

In order to determine whether Pi infusion or composition comprising the same gains an intracellular anti-oxidant activity in cultured astrocytes containing the peroxyl radical generating molecule ABAP, a person skilled in the art may take the following steps:

1. Plate cells in 24 wells plates, astrocytes: 300,000 cells/well (for microglial 130,000 cells/well);
2. For astrocytes: The day after replace medium with fresh medium as described in: Elmann, A., Telerman, A., Mordeohay, S., Erlank, H., Rindner, M., Ofir, R. and Beit-Yannai, E. (2011). Extract of *Achillea fragrantissima* downregulates ROS production and protects astrocytes from oxidative-stress-induced cell death. In: "Neurodegenerative Diseases—Processes, Prevention, Protection and Monitoring", ISBN 978-953-307-485-6, (Raymond Chuen-Chung Chang, ed). InTech Publisher: http://www.intechopen.com/articles/showititle/extract-of-achillea-fragrantissima-downregulates-ros-production-and-protects-astrocytes-from-oxidati;

For microglial cells: 36 hr later replace medium with fresh medium as described in Elmann, A., Mordechay, S., Erlank, H., Telerman, A., Rindner, M., and Ofir, R. 2011 Anti-neuroinflammatory effects of the extract of *Achillea fragrantissima*. BMC Complement Altern Med 11(1):98. http://www.biomedcentral.com/1472-6882/11/98

3. Incubate cells with freshly diluted composition of the invention (1 hr, 5% CO2, 37° C.);
4. Add DCF-DA and incubate cells for additional 30 min (37° C., 5% CO2);
5. Wash twice with PBS;
6. Read "time 0" fluorescence (Ex: 485 nm and Em: 528 nm);
7. Add to cells freshly diluted 2'2'-azobis(2-amidinopropane) dihydrochloride (ABAP, generate peroxyl radicals) to a final concentration of 600 microM, except of "blank" cells (cells w/o antioxidants and w/o ABAP);
8. Read fluorescence at 3, 6, and 24 hr Ex: 485 nm and Em: 528 nm;
9. Measure cell viability 20 hr later using the crystal violet cell staining as described above;
10. A reduction of at least 70% of ROS levels are indication for anti-oxidant activity in the cellular anti-oxidant assay (See Wolfe, K. L., & Liu R. H. (2007) Cellular antioxidant activity (CAA) assay for assessing antioxidants, foods, and dietary supplements. *Journal of Agriculture and Food Chemistry*, Vol. 55, No. 22, pp. 8896-8907.).

Determination of anti-oxidant activity against $ZnCl_2$-induced ROS. In order to determine whether a Pi infusion or composition comprising the same gains an anti-oxidant activity in ZnCl2-treated cultured astrocytes, a person skilled in the art may take the following steps:

1. Produce a primary culture of rat brain glial cells according to the method described in "Protective effects of the essential oil of *Salvia fruticosa* and its constituents on astrocytic susceptibility to hydrogen peroxide-induced cell death". 2009. A. Elmann, S. Mordechay, M. Rindner, O. Larkov, M. Elkebetz, U. Ravid. Journal of agricultural and food chemistry. 57(15):6636-41;
2. Separate astrocytes from other cell types in the culture according to the method described in "Protective Effects of the essential oil of *Salvia fruticosa* and its constituents on astrocytic susceptibility to hydrogen peroxide-induced cell death". 2009. A. Elmann, S. Mordechay, M. Rindner, O. Larkov, M. Elicabetz, U. Ravid. Journal of agricultural and food chemistry. 57(15):6636-41;
3. Plate astrocytes (300,000 cells/0.5 ml/well of 24 wells plate) and incubate (37° C., 5% CO2) for 24 hr as described in: Elmann, A., Telerman, A., Mordechay, S., Erlank, H., Rindner, M., Ofir, R. and Beit-Yannai, E. (2011). Extract of *Achillea fragrantissima* downregulates ROS production and protects astrocytes from oxidative-stress-induced cell death. In: "Neurodegenerative Diseases—Processes, Prevention, Protection and Monitoring", ISBN 978-953-307-485-6, (Raymond Chuen-Chung Chang, ed). InTech Publisher. http://www.intechopen.comiarticlesishow/title/extract-of-achillea-fragrantissima-downregulates-ros-production-and-protects-astrocytes-from-oxidati;
4. Replace growth medium with a fresh one containing 20 micromolars 2'7'-dichlorofluorescein diacetate (DCF-DA);
5. Incubate 30 min (37° C., 5% CO2);
6. Wash twice with PBS;

7. Replace with fresh buffer containing 116 mM NaCl, 1.8 mM CaCl$_2$, 0.8 nM MgSO$_4$, 5.4 mM KCl, 1 mM NaH$_2$PO$_4$, 14.7 mM NaHCO$_3$, and 10 mM HEPES, pH 7.4;
8. Read fluorescence of "time 0" at 485 nm (Extinction) and 520 nm (Emmision).
9. Incubate the cultured cells for hours with freshly diluted composition of the invention;
10. Add freshly diluted ZnCl2 (50 micromolars);
11. Read fluorescence at 1, 2, 3, 4 hr after the addition of ZnCl2 (Ex: 485 nm and Em: 520 nm).
12. A reduction of at least 60% of ROS levels are indication for the anti-oxidant activity in this assay.

Determination of GDNF Induction by Pi.

In order to determine whether Pi infusion or composition comprising the same gains an inducing activity of GDNF in astrocytes, a person skilled in the art may take the following steps:
1. Produce a primary culture of rat brain glial cells according to the method described in "Protective effects of the essential oil of *Salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
2. Separate astrocytes from other cell types in the culture according to the method described in "Protective effects of the essential oil of *Salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
3. Replace astrocytes at 6 well PDL-coated plastic plates at a density of 2*10$^6$/well, in DMEM/F12 containing 5% FBS, 2 mM glutamine, 100 U/ml penicillin, and 100 micrograms/ml streptomycin.
4. Twenty four hr after plating, aspirate the original medium from the plate, and add fresh medium to the cells.
5. Incubate the cultured cells for 9-24 (is it OK to give range? it is from the article FIG. 9) hours with freshly diluted infusion of the invention;
6. Harvest the cells using RLT buffer containing 1% beta mercaptoethanol.
7. Extract RNA by the RNeasy Plus Minin Kit (Qiagen) according to the manufacturer's instructions.
8. Remove genomic DNA from RTNA samples by using 50 units of RNase-free DNaseI at 37° C. for 1 h.
9. Convert RNA (20 micrograms) to cDNA using the Thermo Scientific Versa cDNA kit following the manufacturer's protocol.
10. Use the cDNA for quantitative real-time PCR amplification with TaqMan chemistry (Applied Biosystems) using Rat GDNF predesigned TaqMan Gene Expression. Assay from Applied Biosystems (Assay ID Rn00569510).
11. Normalize values relative to rat glyceraldehydes-3-phosphate dehydrogenase (GAPDH; Assay ID Rn00569510).
12. Use the data created by the ABI PRISM 7700 Sequence Detection System (using version 1.6 software).
13. An induction of 5-12 (is it OK to give range? it is from the article—FIG. 9) of GDNF levels are indication for the inducing activity in this assay.

Determination of Anti-Inflammatory Activity of Pi (Cytokine Inhibition).

In order to determine whether a Pi infusion or composition comprising the same gains an anti-inflammatory activity in LPS-activated microglial cells, a person skilled-in the art may take the following steps:
1. Prepare a primary culture of microglial cells as described in "Anti-neuroinflammatory effects of geranium oil in microglial cells" 2010. A. Elmann, S. Mordechay, M. Rindner, Ravid. Journal of functional foods, 2:17-22;
2. Plate microglial cells (3.5×10$^4$ cells/well) on a 24-well tissue culture plate, in DMEM containing 10% PBS, 2 mM glutamine, 100 U/ml penicillin and 100 micrograms/ml streptomycin;
4. Treat cells with freshly diluted composition of the invention;
5. Activate microglial cells with lipopolysaccharide (EPS, 100 nanograms/ml);
6. Collect conditioned media after 24 hr for the measurement of IL-1β and IL-6 levels;
7. Measure the levels of cytokines by ELISA;
8. Inhibition higher than 60% of the induced IL-6 and of 90% of the induced IL-1β are an indication for anti-inflammatory activity in this model;

Determination of Anti-Inflammatory Activity of Pi (Glutamate Inhibition).

In order to determine whether Pi infusion or composition comprising the same gains an anti-inflammatory activity in LPS-activated microglial cells, a person skilled in the art may take the following steps:
1. Prepare a primary culture of microglial cells as described in "Anti-neuroinflammatory effects of geranium oil in microglial cells" 2010. A. Elmann, S. Mordechay, M. Rindner, U. Ravid. Journal of functional foods. 2:17-22;
2. Plate microglial cells (3.5×10$^4$ cells/well) on a 24-well tissue culture plate, in DMEM containing 10% FBS, 2 mM glutamine, 100 U/ml penicillin and 100 micrograms/ml streptomycin;
4. Treat cells with freshly diluted composition of the invention;
5. Activate microglial cells with lipopolysaccharide (LPS, 100 nanograms/ml);
6. Collect conditioned media after 24 hr for the measurement of glutamate levels;
7. Measure the levels of glutamate by a colorimetric enzymatic assay kit (glutamate assay kit, BioVision, CA, USA)
8. Inhibition higher than 75% of the induced, glutamate is an indication for anti-inflammatory activity in this model;

Determination of Anti-Inflammatory Activity of Pi (Induced NO Inhibition).

In order to determine whether PI infusion or composition comprising the same gains an anti-inflammatory activity in LPS-activated microglial cells, a person skilled in the art may take the following steps:
1. Prepare a primary culture of microglial cells as described in "Anti-neuroinflammatory effects of geranium oil in microglial cells" 2010. A. Elmann, S. Mordechay, M. Rindner, U. Ravid. Journal of functional foods. 2:17-22;
2. Plate microglial cells (1×10$^5$ cells/well) on a 24-well tissue culture plate, in RPMI-1640 without phenol red, containing 2% FBS, 2 mM glutamine, 1 mM sodium pyruvate, 50 micromolars beta mercaptoethanol, 100 U/ml penicillin and 100 micrograms/ml streptomycin;
4. Treat cells with freshly diluted composition of the invention;
5. Activate microglial cells with lipopolysaccharide (LPS, 5 nanograms/ml);
6. Collect conditioned media after 20 hr for the measurement of NO levels;
7. Measure the levels of NO by Griess reagent;

8. Inhibition higher than 80% of the induced NO is an indication for anti-inflammatory activity in this model;

Determination of Viability of Cells treated with Pi.

In order to determine whether Pi infusion or composition comprising the same is not toxic to LPS-activated microglial cells, a person skilled in the art may take the following steps:
1. Prepare a primary culture of microglial cells as described in "Anti-neuroinflammatory effects of geranium oil in microglial cells" 2010. A. Elmann, S. Mordechay, M. Rindner, U. Ravid. Journal of functional foods. 2:17-22;
2. Plate microglial cells ($3.5 \times 10^4$ cells/well) on a 24-well tissue culture plate, in DMEM containing 10% FBS, 2 mM glutamine, 100 U/ml penicillin and 100 micrograms/ml streptomycin;
4. Treat cells with freshly diluted composition of the invention;
5. Activate microglial cells with lipopolysaccharide (LPS, 100 nanograms/ml);
6. Collect conditioned media after 24 hr for different assays (e.g. cytokines or glutamate levels) and measure cell viability by the crystal violet cell staining as follows:
7. Transfer plate to a chemical hood;
8. Dispense 150 µl 5% formaldehyde (in PBS) to each well and incubate 15 min at RT;
9. Pour out formaldehyde to chemical waste and gently rinse under running tap water;
10. Remove excess water by tapping plate on a tissue paper;
11. Dispense 150 µl crystal violet solution (10 gr/liter, in water) to each well;
12. Incubate 15 min at RT (in the chemical hood);
13. Pour out crystal violet to chemical waste and gently rinse under running tap water until all residual dye is removed;
14. Tap plate on a tissue paper to remove remaining water;
15. Dispense 150 µl 33% aqueous glacial acetic acid to each well;
16. Measure absorbance using a microplate reader at 540 nm with 690 nm reference filter.
17. Viability which is not lower than the viability of LPS-treated cells is considered as not toxic in this assay.

Determination of Inhibition of SAPK/JNK-Activation by Pi.

In order to determine whether Pi infusion or composition comprising the same gains an inhibitory activity against $H_2O_2$-induced SAPK/JNK activation in cultured astrocytes, a person skilled in the art should follow the following steps:
1. Produce a primary culture of rat brain glial cells according to the method described in "Protective effects of the essential oil of *Salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
2. Separate astrocytes from other cell types in the culture according to the method described in "Protective effects of the essential oil of *Salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
3. Incubate the cultured astrocytes (37° C., 5% CO2) for 2 hours with freshly diluted composition of the invention;
4. Add 175 micromolars of freshly diluted $H_2O_2$;
5. Incubate the culture for 40 min (37° C., 5% CO2);
6. Prepare cell homogenates and measure protein levels.
7. Measure the amount of total and phosphoSAPK/JNK in cell lysates (5.5 micrograms of protein) of astrocytes, by ELISA using the PathScan total SAPK/JNK sandwich ELISA kit (Cell Signaling TECHNOLOGY) and the PathScan phosoho-SAPK/JNK (Thr183/Tyr185) sandwich ELISA kit (Cell Signaling TECHNOLOGY), respectively, according to the manufacturer's instructions. Determine the optical density at 450 nm using a microplate reader.

Determination of Inhibition of ERK 1/2-Activation by Pi.

In order to determine whether Pi infusion or composition comprising the same gains an inhibitory activity against $H_2O_2$-induced ERK 1/2 activation in cultured astrocytes, a person skilled in the art should follow the following steps:
1. Produce a primary culture of rat brain glial cells according to the method described in "Protective effects of the essential oil of *Salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
2. Separate astrocytes from other cell types in the culture according to the method described in "Protective effects of the essential oil of *Salvia fruticosa* and its constituents on astrocytic susceptibility to hydrogen peroxide-induced cell death". 2009. A. Elmann, S. Mordechay, M. Rindner, O. Larkov, M. Elkabetz, U. Ravid. Journal of agricultural and food chemistry. 57(15):6636-41;
3. Incubate the cultured astrocytes (37° C., 5% CO2) for 2 hours with freshly diluted composition of the invention;
4. Add 175 micromolars of freshly diluted $H_2O_2$;
5. Incubate the culture for 40 min (37° C., 5% CO2);
6. Prepare cell homogenates and measure protein levels.
7. Measure the amount of phosphoERK 1/2 in cell lysates (5.8 micrograms) of astrocytes, by ELISA using the PathScan phosoho-p44/42 MAPK (Thr202/Tyr204) sandwich ELISA kit (Cell Signaling TECHNOLOGY). Determined the optical density at 450 nm using a microplate reader.

EXAMPLES

In order to illustrate the invention, the following examples are included. However, it is to be understood that these examples do not limit the invention and are only meant to suggest a method of practicing the invention.

Materials.

For the following examples, Dulbecco's Modified Eagle's Medium (DMEM), Leibovitz-15 medium, glutamine, antibiotics (10,000 IU/mL penicillin and 10,000 µg/mL streptomycin), soyabean trypsin inhibitor and fetal bovine serum (FBS) were purchased from Biological Industries (Beit Haemek, Israel); Dimethyl sulphoxide (DMSO) was obtained from Applichem (Darmstadt, Germany); and hydrogen peroxide ($H_2O_2$) was obtained from MP Biomedicals (Ohio, USA). $ZnCl_2$, 2,2-Diphenyl-1-picrylhydrazyl (DPPH) and 2'7'-dichlorofluorescein diacetate (DCF-DA) were purchased from Sigma-Aldrich Chemical Co. (St Louis, Mo., USA). 2,2'-Azobis(amidinopropane) (ABAP) was obtained from Wako chemicals (Richmond, Va.).

Experimental Animals.

For the following examples, newborn Wistar rats (0-2 days old) were obtained from Harlan Laboratories. The experiments were performed in compliance with the appropriate laws and institutional guidelines, and were approved by the Institutional Animal Care and Use committee of the Volcani Center, Agricultural Research Organization (Number IL-135/07).

Data Analysis.

For the following examples, statistical analyses were performed with one-way ANOVA followed by Tukey-Kramer multiple comparison tests using Graph Pad InStat 3 for windows (GraphPad Software, San Diego, Calif., USA).

Determination of the Free Radical Scavenging Activity in the DPPH Assay.

For the following examples, antioxidant activity was measured using the 2,2-diphenyl-1-picryhydrazyl DPPH radical scavenging assay. Different dilutions of the infusion (0.15 mL) were added to 1 mL of DPPH (3.9 mg/100 mL methanol) in test tubes wrapped in aluminum foil. Absorbance (A) was measured at 517 nm after 15 min incubation in the dark. All measurements were made with distilled water as blank. The scavenging ability (%) of the samples was calculated as $(A_{control}-A_{sample})/A_{control} \times 100)$.

Preparation of Primary Astrocytes Cultures in the Following Examples.

Cultures of primary rat astrocytes were prepared from cerebral cortices of 1- to 2-day-old neonatal Wistar rats. Briefly, meninges and blood vessels were carefully removed from cerebral cortices kept in Leibovitz-15 medium; brain tissues were dissociated by trypsinization with 0.5% trypsin (10 min, 37° C., 5% $CO_2$); and cells were washed first with DMEM containing soybean trypsin inhibitor (100 µg/mL) and 10% FBS and then with DMEM containing 10% FBS. Cells were seeded in tissue culture flasks pre-coated with poly-D-lysine (PDL, 20 µg/mL in 0.1 M borate buffer pH 8.4) and incubated at 37° C. in humidified air with 5% $CO_2$. The medium was changed on the second day and every second day thereafter. At the time of primary cell confluence (day 10), microglial and progenitor cells were discarded by shaking (180 RPM, 37° C.) for 24 h. Astrocytes were then re-plated on 24-well PDL-coated plastic plates, (a) for toxicity assays, at a concentration of $1 \times 10^5$/well, in DMEM (without phenol red) containing 2% FBS, 2 mM glutamine, 100 U/mL penicillin, and 100 µg/mL streptomycin. (b) For the cellular antioxidant activity assay at a concentration of $3 \times 10^5$/well, in DMEM containing 10% FBS 8 mM HEPES, 2 mM glutamine, 100 U/mL penicillin, and 100 µg/mL streptomycin.

Treatment of Astrocytes in the Following Examples.

Twenty four hours after plating, the original medium in which the cells were grown was aspirated off, and fresh medium was added to the cells. Dilutions of Pi infusion, ABAP, DCF-DA, Zinc and of $H_2O_2$ in the growth medium were made freshly from stock solutions prior to each experiment and were used immediately.

Evaluation of Intracellular ROS Production in the Following Examples.

Intracellular ROS production was detected using the non-fluorescent cell permeating compound, 2',7'-dichlorofluorescein diacetate (DCF-DA). DCF-DA is hydrolyzed by intracellular esterases and then oxidized by ROS to a fluorescent compound 2'-7'-DCF. Astrocytes were plated onto 24 wells plates (300,000 cells/well) and treated with DCF-DA (20 µM) for 30 min at 37° C. Following incubation with DCF, cultures were rinsed twice with PBS and then re-suspended (1) For measurement of $H_2O_2$-induced ROS: in DMEM containing 10% FBS, 8 mM HEPES, 2 mM glutamine, 100 U/ml penicillin, and 100 µg/mL streptomycin (2) For measurement of $ZnCl_2$-induced ROS: in a defined buffer containing 116 mM NaCl, 1.8 mM $CaCl_2$, 0.8 mM $MgSO_4$, 5.4 mM KCl, 1 mM $NaH_2PO_4$, 14.7 mM $NaHCO_3$, and 10 mM HEPES, pH, 7.4. The fluorescence was measured in a plate reader with excitation at 485 nm and emission at 520 nm.

Example 1. Pi Infusion Protects Astrocytes from $H_2O_2$-Induced Cell Death in a Dose-Dependent Manner Astrocytes were treated with different concentrations of a Pi infusion. $H_2O_2$ was added 2 h after the addition of the Pi infusion and cell death was determined 20 h later. The results are means±SEM of four experiments (n=16). **p<0.001.

Example 2. Time-Course of the Protective Effect of the Pi Infusion on Astrocytes Astrocytes were pre-incubated with the Pi infusion (100 µg/mL) for 2 h. $H_2O_2$ was then added and cytotoxicity was measured at the indicated time points. The results are the means±SEM of four experiments=16). p<0.01 *p<0.001 Compared to cells treated with $H_2O_2$ only.

Example 3. Pre-Incubation of Astrocytes with Pi Infusion is a Prerequisite for the Protective Effect Against $H_2O_2$ Cytotoxicity Pi infusion (12.5 µg/mL) was added to astrocytes before (−2 h, −1 h) or after (1 h, 2 h) the addition of $H_2O_2$. Cytotoxicity was measured 20 h later. The results are means±SEM of one experiment (n=4) out of three independent experiments. **p<0.001 *p<0.01

Example 4. Pi Infusion Attenuates $H_2O_2$-Induced ROS Production in Astrocytes

Astrocytes were pre-loaded with the redox-sensitive DCF-DA for 30 min and washed with PBS. Pre-loaded astrocytes were then pre-incubated with various concentrations of Pi infusion for 2 h. $H_2O_2$ (175 µM) was added to the culture and the fluorescence intensity representing ROS production was measured. A. The fluorescence levels of cells that had been pre-incubation with 100 µg/mL Pi extract were measured at the indicated time points. *p<0.05 p<0.01 *p<0.001 Compared to cells treated with $H_2O_2$ only B. The fluorescence levels of cells that had been pre-incubated with various concentrations of Pi extract were measured after 3 h. Each point represents the mean±SEM of two experiments (n=8). *p<0.05 p<0.01 *p<0.001.

Example 5. Zinc Induces ROS Generation and the Pi Infusion-Attenuates ROS Production Following Treatment of Astrocytes with Zinc Astrocytes were pre-loaded with DCF-DA for 30 min and washed with PBS. They were then pre-incubated for 2 h with various concentrations of Pi infusion. Then, $ZnCl_2$ (50 µM) was added and the resulting fluorescence signal was measured at the indicated time points. The results represent means±SEM of two experiments (n=8).

*p<0.05 ***p<0.001 compared to cells treated with zinc alone.

Example 6. Pi Infusion is Similarly Effective in Attenuating ROS Production when Applied Before or After $H_2O_2$ Pi infusion (12.5 µg/mL) was added to astrocytes before (−2 h, −1 h) or after (1 h, 2 h) the addition of $H_2O_2$. ROS levels in DCF-DA pre-loaded astrocytes were measured 1, 4 and 6 h after the application of $H_2O_2$. The results are means±SEM of two experiments (n=6). **p<0.001.

Example 7. Peroxyl Radical-Induced Oxidation of DCFH to DCF in Primary Astrocytes and the Inhibition of Oxidation by the Pi Infusion. A Astrocytes were incubated for 1 h with Pi infusion. Then, the astrocytes were pre-loaded with DCF-DA for 30 min and washed. ASAP (0.6 mM) was added to the culture and the fluorescence intensity representing ROS levels was measured. A. The fluorescence levels of cells that had been pre-incubation with 100 µg/mL Pi extract were measured at the indicated time points. ***p<0.001 compared to cells treated with ABAP only. B. The fluorescence levels of cells that had been pre-incubated with various concentrations of Pi extract were measured at the indicated time points. The results represent means±SEM of three experiments (n=12). *p<0.05 p<0.01 *p<0.001.

Example 8. DPPH Radical Scavenging Activity of the Pi Infusion

The free-radical scavenging activity of the Pi infusion was determined by the 2,2-diphenyl-1-picryhydrazyl (DPPH) radical which is considered to be a model lipophilic radical. Pi infusion was found to be a very potent free-radical scavenger with an $IC_{50}$ value of 45 µg/mL and 80% inhibition of DPPH absorbance at 517 nm (FIG. 8). The concentration of the infusion was 10 mg/mL. **p<0.001.

Example 9. Treatment with the Pi Infusion Increases the Levels of GDNF Transcript in Primary Astrocytes Astrocytes were replaced at 6-well PDL-coated plastic plates at a density of $2\times10^6$/well, in DMEM/F12 containing 5% PBS, 2 mM glutamine, 100 U/mL penicillin, and 100 µg/mL streptomycin. Twenty four hr after plating, the original medium of the cells was aspirated off and fresh medium was added to the cells. Cells were then lysed and collected using RLT buffer containing 1% βME for RNA extraction.
2.9. Quantitative Real-Time PCR Analysis.
RNA was extracted by the RNeasy Plus Mini Kit (Oiagen, Hilden, Germany) according to the manufacturer's instructions, Genomic DNA was removed from the RNA samples by using 50 units of RNase-free DNaseI at 37° C. for 1 h. RNA (20 µg) was converted to cDNA using the Thermo Scientific Verso cDNA kit (Thermo Fisher Scientific Inc) following the manufacturer's protocol. The cDNA was used for quantitative real-time PCR amplification with TaqMan chemistry (Applied Biosystems) using Rat¯GDNF pre-designed. TaqMan Gene Expression Assay from Applied Biosystems (Assay ID Rn00569510). Values were normalized relative to Rat glyceraldehyde-3-phosphate dehydrogenase (GAPDH; Assay ID Rn00569510). All results from three technical replicates were normalized to GAPDH and express as relative expression ratios calculated (relative quantity, RQ) using the comparative method and based on the data that were created by the ABI PRISM 7700® Sequence Detection System (using version 1.6 software).
Rat primary astrocytes were exposed to 250 µg/mL of Pi infusion for 9 or 24 h. Total RNA was then extracted. GDNF transcripts were measured using quantitative real-time PCR. The results of three technical replicates were normalized to glyceraldehyde-3-phosphate (GAPDH) and are expressed as relative quantities of GDNF transcripts. The results are means±SD of one out of three experiments. Means-paired, one-tailed t-tests were used to evaluate the effects of the infusion on the expression of GDNF and the effect of the duration of the incubation. These tests yielded P(t) values of 0.029 and 0.105, respectively. Therefore, inventors can conclude that, in cases in which the effect of the duration is not statistically significant, the effect of the Pi infusion is significant at a 95% significance level.

Example 10. Different Extracts of Pi Protect Astrocytes from $H_2O_2$-induced Cell Death—a Comparison between the Infusion and the Ethanolic Extracts Prepared from the Wild or the Cultivated Plant Astrocytes were preincubated for 2 hr with different amounts of ethanolic extract (A) or infusion (B) prepared from either wild type or cultivated Pi. $H_2O_2$ was added and cytotoxicity was measured 20 hr later.

Figure 15:
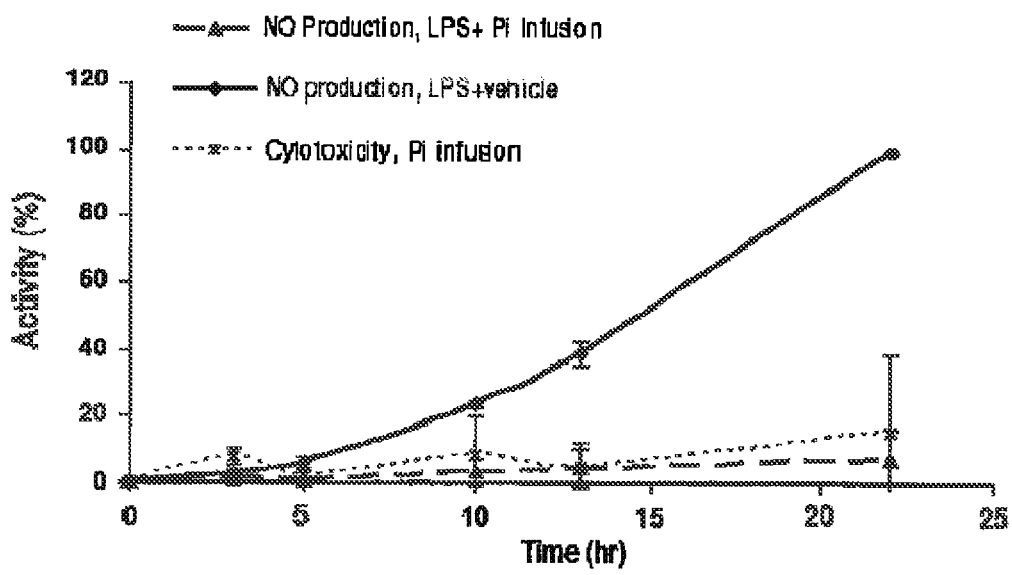
FIG. 15 shows kinetics of LPS-induced NO production in the presence and absence of Pi infusion.

Example 11. Kinetics of LPS-Induced NO Production in the Presence and Absence of Pi Infusion Microglial cells were pretreated with Pi infusion (400 µg/ml). LPS was then added and NO production and cytotoxicity were measured at the indicated time points. The results are the mean±SD of 2 experiments (n=2). FIG. 15 shows that difference in NO production between presence and absence of Pi infusion becomes more significant as time advances.

Example 12. Inhibition of NO Production in Activated Microglial Cells in Response to Pi Infusion—a Comparison Between the Wild and the Cultivated Plant Microglial cells were incubated for 2 hr with different amounts of an infusion prepared from either wild type or cultivated Pi and were activated by LPS. NO was determined using Griess reagent 20-24 hr later. FIG. 16 shows that cultivated Pi infusion inhibited NO production in activated microglial cells.

Example 13. DPPH Radical Scavenging Activity of Pi Infusion Compared to Memantine, Quercetin and Vitamin C The DPPH scavenging ability of Pi infusion, memantine, quercetin and vitamin C were compared for eight minutes. The results are presented in FIG. 19 as means±SD (n=2).

Example 14. Pi Infusion Suppresses $H_2O_2$-Induced SAPK/JNK Phosphorylation in Astrocytes In this example, enzyme-linked immunosorbent assays (ELISA) for total and phospho-SAPK/JNK was performed. To measure the amount of total and phosphoSAPK/JNK in cell lysates of astrocytes, ELISA was performed according to the manufacturer's protocol using the PathScan total SAPK/JNK sandwich ELISA kit (Cell Signaling TECHNOLOGY) and the PathScan phospho-SAPK/JNK (Thr183/Tyr185) sandwich ELISA kit (Cell Signaling TECHNOLOGY), respectively. Astrocytes were treated with 175 µM of $H_2O_2$ for 40 min following preincubation with Pi infusion for 2 h. The levels of phosphorylated and total SAPK/JNK were measured by ELISA. tSAPK/JNK is total amount of SAPK/JNK in the cell. pSAPK/JNK is the phosphorylated form. According to FIG. 20A, Pi infusion suppresses $H_2O_2$-induced SAPK/JNK phosphorylation in astrocytes.

It is apparent that the total amount of SAPK/JNK does not change with the treatment. The phosphorylated form is induced following a signal.

Example 15. The Affect of Pi Infusion an $H_2O_2$-Induced Phosphorylation of ERK 1/2 in Astrocytes Enzyme-linked immunosorbent assays (ELISA) for phospho-ERK(phospho-p44/42 MAPK) was performed. To measure the amount of phospho-ERK 1/2 (i.e. phospho-p44/42 MAPK) in cell lysates of astrocytes, ELISA was performed according to the manufacturer's protocol using the PathScan phospho-p44/42 MAPK (Thr202/Tyr204) sandwich ELISA kit (Cell Signaling TECHNOLOGY). The optical density was determined at 450 nm using a microplate reader. Astrocytes were treated with 175 µM of $H_2O_2$ for 40 min following preincubation with Pi infusion for 2 h. The levels of phosphorylated ERK 1/2 were measured by ELISA. FIG. 21 shows the affect of Pi infusion on $H_2O_2$-induced phosphorylation of ERK 1/2 in astrocytes. According to FIG. 21, there is only minor effect on ERK1,2 phosphorylation in $H_2O_2$-treated astrocytes.

Figure 22:
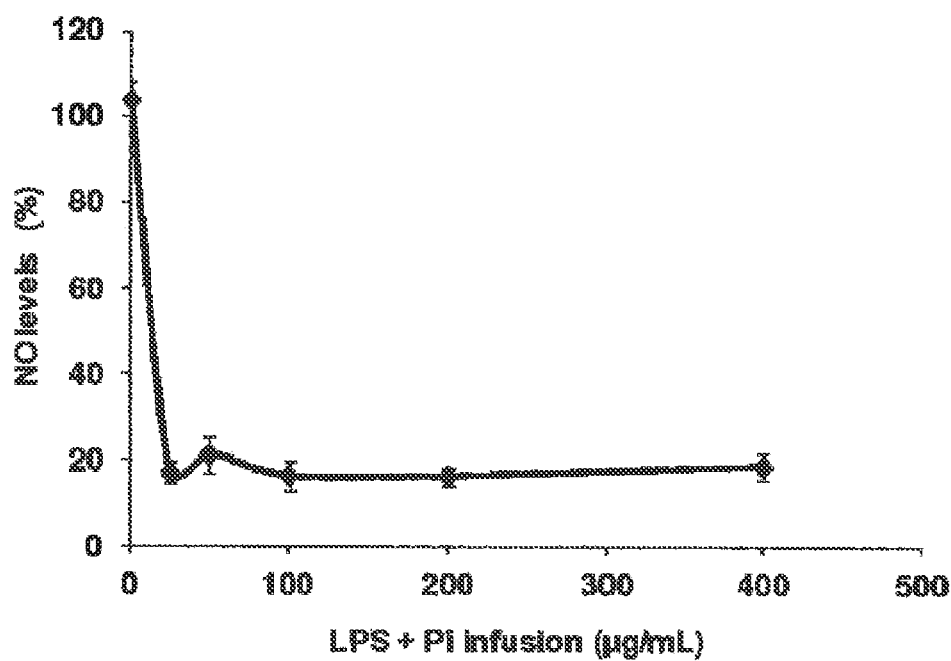
FIG. 22 shows inhibition of NO production by LPS-activated microglial cells in response to Pi infusion.

Example 16. Inhibition of NO Production by Activated Microglial Cells in Response to Pi Infusion Microglial cells were treated with different concentrations of the infusion and concomitantly activated by LPS (4.5 ng/mL). NO levels in cell conditioned supernatants were measured 20 h later. The results (activity as % of untreated LPS-activated cells) represent means±SEM of 2 separate experiments (n=8). FIG. 22 shows that Pi infusion inhibits NO production in activated microglial cells.

Figure 23:
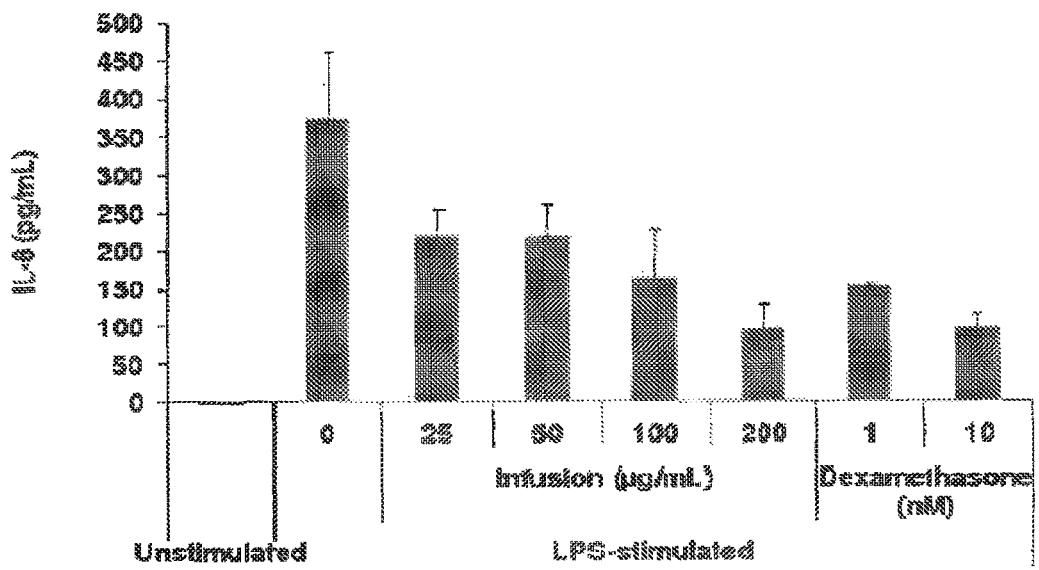
FIG. 23 shows that Pi infusion down-regulates IL-6 secretion from activated microglial cells. A comparison with an anti-inflammatory drug dexamethasone.

Example 17. Pi Infusion Down-Regulates IL-6 Secretion from Activated Microglial Cells Microglial cells were treated with the indicated concentrations of Pi infusion, followed by stimulation with LPS (100 ng/mL). After 24 h, conditioned media were collected and tested for cytokine levels by ELISA. IL-6 levels in the activated cells (designated as 100%) were 373 pg/mL. Data represent the means±SEM of two independent experiments (n=4). FIG. 23 shows that Pi infusion down-regulates IL-6 secretion from activated microglial cells.

Figure 24:
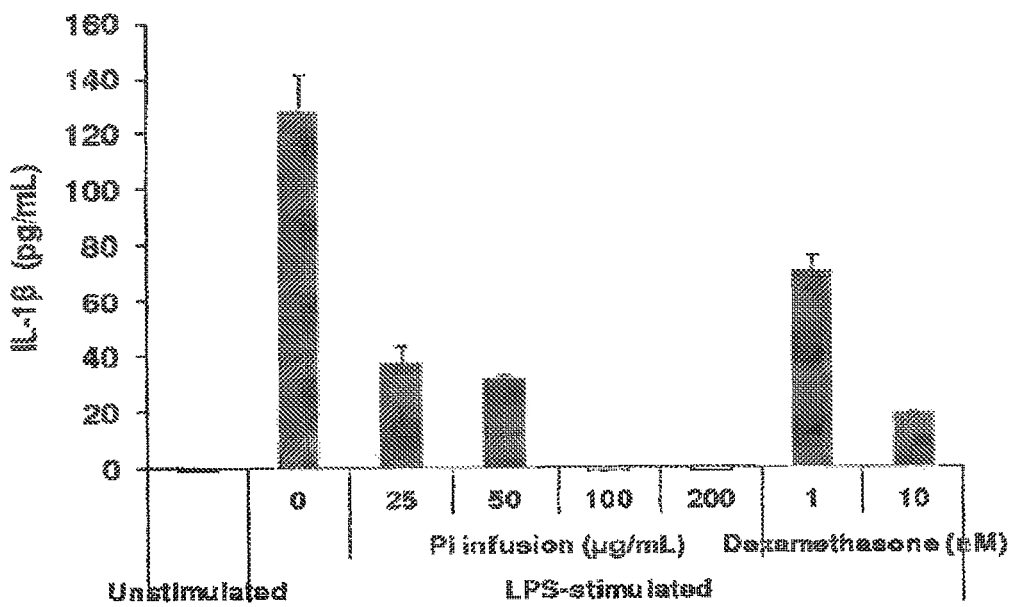
FIG. 24 shows that Pi infusion down-regulates IL-1β secretion from activated microglial cells. A comparison with an anti-inflammatory drug dexamethasone.

Example 18. Down-Regulation of IL-1β Transcription and Secretion by LPS-Stimulated Microglial Cells by Pi Infusion Microglial cells (5×10$^6$ cells) were treated with 100 µg/mL of Pi infusion, followed by stimulation with LPS. Total RNA was extracted and levels of IL-1β transcripts were measured using quantitative real-time PCR. The results of three technical replicates were normalized to alpha-tubulin transcripts and are expressed as relative quantities of IL-1β transcripts. The results are means±SD of one out of three experiments. Microglial cells were treated with the indicated concentrations of Pi infusion, followed by stimulation with LPS (100 ng/mL). After 24 h, conditioned media were collected and tested for cytokine levels by ELISA. IL-1β levels in the activated cells (designated as 100%) were 128 pg/mL. Data represent the means±SEM of two independent experiments (n=4). It is apparent from FIG. 24 that Pi infusion down-regulates IL-1β secretion from activated microglial cells.

Figure 25:
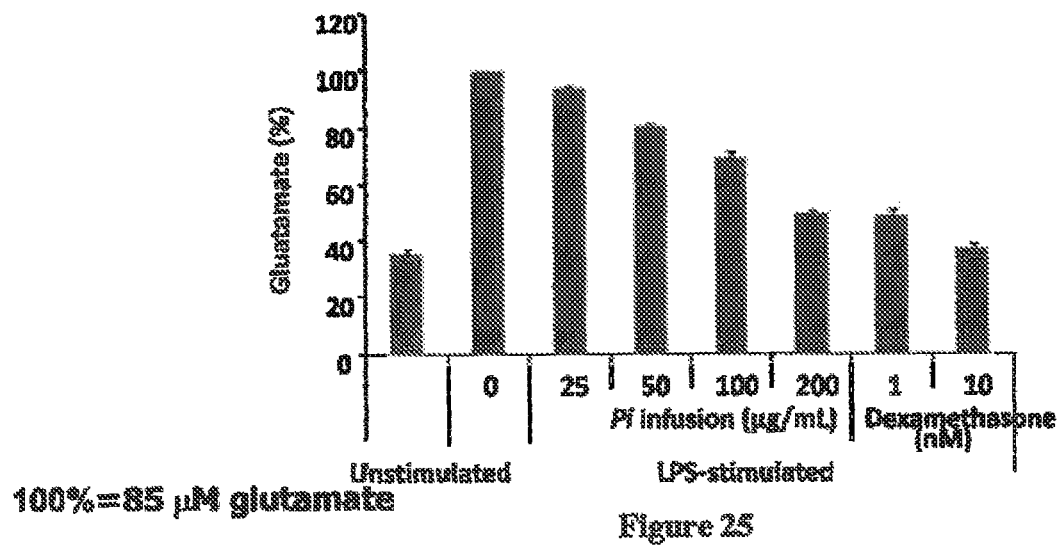
FIG. 25 shows that Pi infusion down-regulates glutamate secretion from activated microglial cells. A comparison with an anti-inflammatory drug dexamethasone.
Figure 26:
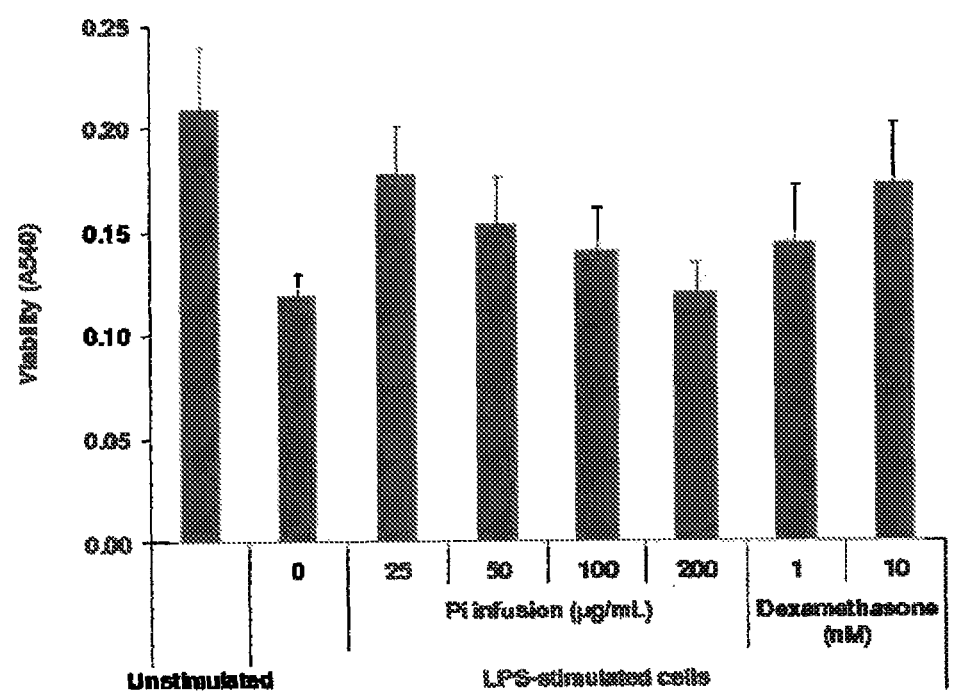
FIG. 26 shows that the reduction in inflammatory parameters is not a result of a cytotoxic effect.

Example 19. Down-Regulation of Glutamate Secretion from Activated Microglial Cells by Pi Infusion Microglial cells were treated with the indicated concentrations of Pi infusion, followed by stimulation with LPS (100 ng/mL). After 24 h, conditioned media were collected and tested for: (A) glutamate levels by a commercial kit Glutamate levels in the activated cells (designated as 100%) were 85 µM. (B) cell viability by the crystal violet staining. Data represent the means±SEM of three independent experiments (n=6). FIG. 25 shows that Pi infusion down-regulates glutamate secretion from activated microglial cells. FIG. 26 shows that the reduction in inflammatory parameters was not a result of a cytotoxic effect.

Example 20. Pi Infusion Prevents the Glutamate-Induced Neuronal Cell Death

Figure 27:
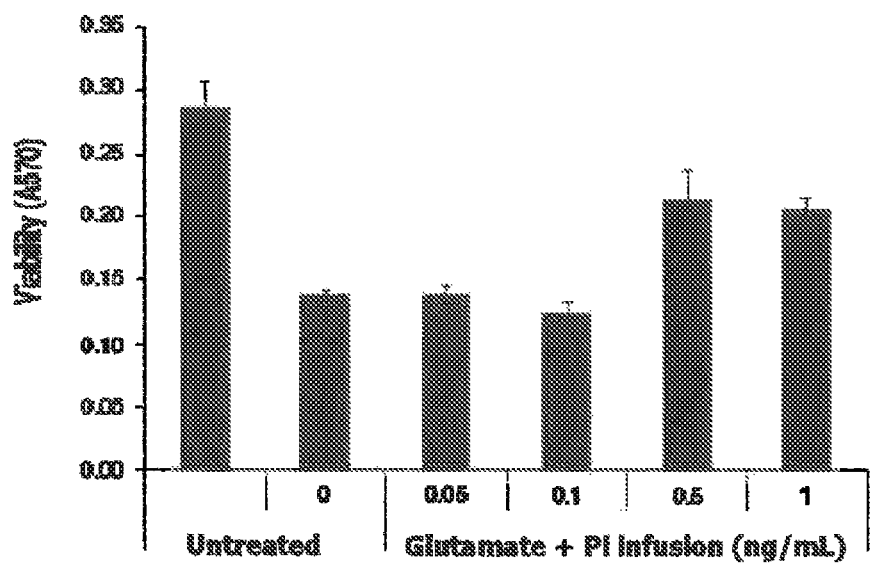
FIG. 27 shows that Pi infusion prevents the glutamate-induced neuronal cell death.
Figure 28:
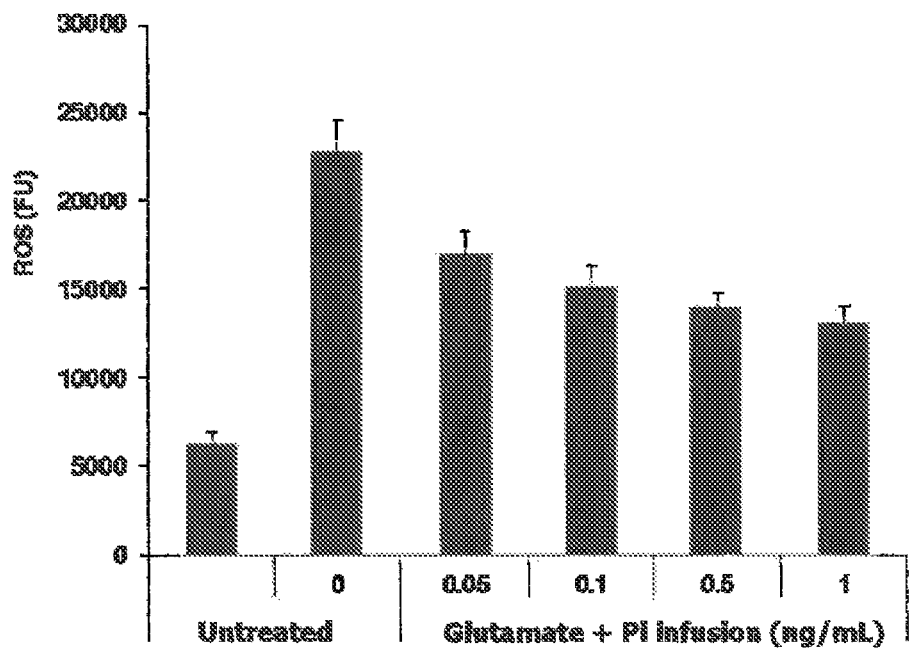
FIG. 28 shows that Pi infusion prevents reactive oxygen species (ROS) elevation in glutamate treated neuronal cells.

N2a neuronal cells were treated with glutamate (100 µM) and different concentrations of Pi infusion. Viability (FIG. 27) and ROS levels (FIG. 28) were measured 20 hr later. The results are the mean±SEM of one experiment with seven replicates. FIGS. 27 and 28 show that Pi infusion prevents the glutamate-induced neuronal cell death.

Viability:

N2a cells were plated (5000 cells/well) in 96 wells plates in a medium composed of 45% Opti-MEM, 50% DMEM, 1% fetal bovine serum, 2 mM glutamine, penicillin and streptomycin. The day after, the medium was changed to fresh medium, and cells were concomitantly treated with glutamate (100 micromolars) and different concentrations of Pi infusion. Twenty hr later, viability was determined using the MTT (3-[4,5-dimethylthiazole-2-yl]2,5-diphenyl tetrazolium bromide) method. MTT was added to a final concentration of 0.5 mg/ml to each well and the plates were returned to the incubator for 3 hr. At the end of the incubation, an a solution of Isopropanol, HCl and Triton X-100 (to final concentrations of 89%, 1% and 10%, respectively) was added to the cells. Components of the wells were mixed until the formazan crystals were completely dissolved, and absorbance was measured at 570 nm using a plate reader.

ROS:

N2a cells were plated (10,000 cells/well) in 96 wells plates in a medium composed of 45% Opti-MEM, 50% DMEM, 1% fetal bovine serum, 2 mM glutamine, penicillin and streptomycin. The day after, DCF-DA (20 micromolars) were added to the cells for 30 min at 37° C. Then, cultures were rinsed twice with PBS, fresh medium was added to the cells, and cells were concomitantly treated with glutamate (100 micromolars) and different concentrations of Pi infusion. Twenty hr later, fluorescence, which indicates ROS levels, was measured by a plate reader with excitation at 485 nm and emission at 520 nm.

Treatment with Pi infusion (Concentrations higher then 0.5 ng/ml) provided 50% protection against glutamate toxicity.

Treatment of neuronal cells with glutamate causes elevation in ROS levels, and treatment with Pi infusion (1 ng/ml) inhibits 58% of the induced ROS levels.

Example 21. Reduction of Glutamate-Induced ROS by Pi Infusion—Concomitant Addition of Pi Infusion and Glutamate is More Efficient than Preincubating Neuronal Cells with Pi Infusion Before Glutamate Treatment Pi infusion (0.5 or 1 ng/ml) was added to N2a neuronal cells two hr before (−2) or concomitant with (0) the addition of glutamate (100 μM). ROS levels were measured 20 hr later. The results are the mean±SEM of one experiment with seven replicates.

N2a cells were plated (10,000 cells/well) in 96 wells plates in a medium composed of 45% Opti-MEM, 50% DMEM, 1% fetal bovine serum, 2 mM glutamine, penicillin and streptomycin. Fourty eight hr later, DCF-DA (20 micromolars) was added to the cells for 30 min at 37° C. Then, cultures were rinsed twice with PBS, fresh medium was added to the cells, and cells were either treated with Pi infusion two hr before or concomitantly treated with glutamate (100 micromolars). Twenty hr later, fluorescence, which indicates ROS levels, was measured by a plate reader with excitation at 485 nm and emission at 520 nm.

Figure 29:
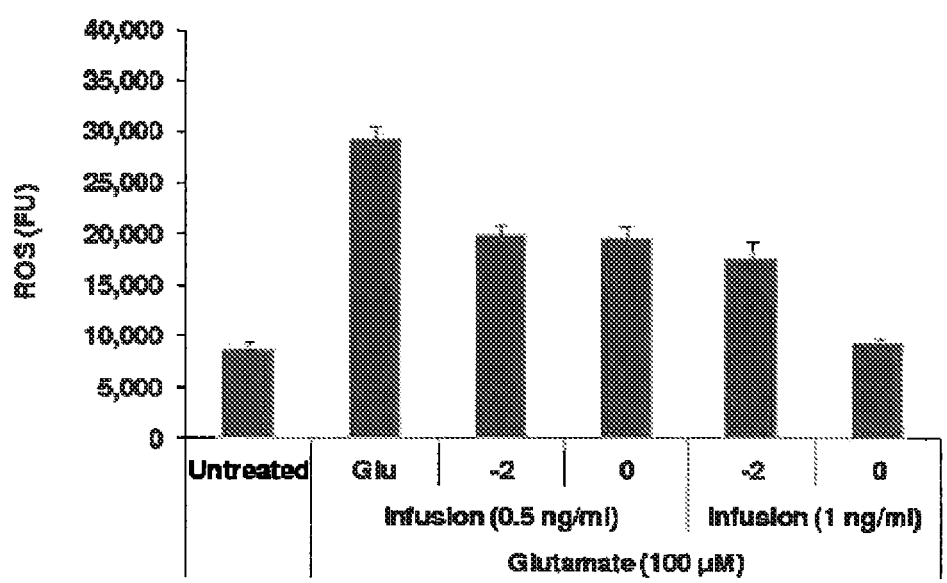
FIG. 29 shows that Pi infusion is more effective in attenuating glutamate-induced ROS production when applied concomitantly with glutamate.

FIG. 29 shows that treatment of neuronal cells with glutamate causes a 3.4 fold elevation in ROS levels, and concomitant treatment with Pi infusion (1 ng/ml) inhibits 97% of the induced ROS levels. Pre-treating the cells with the same concentration of Pi infusion was less effective, and inhibited only 56% of the induced ROS levels.

Figure 30A:
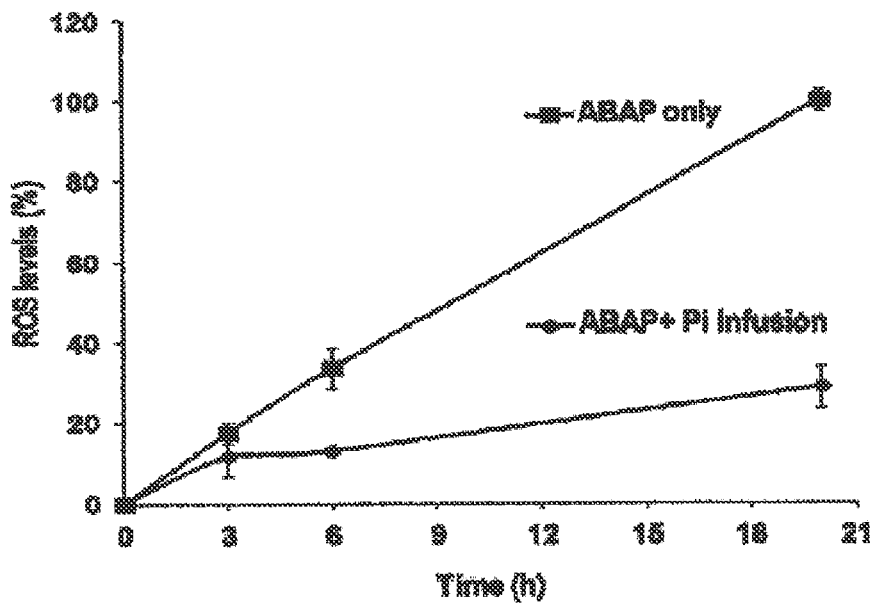
FIG. 30 shows that ABAP-induced peroxyl radical elevation in primary microglial cells is inhibited by Pi infusion.
Figure 30B:
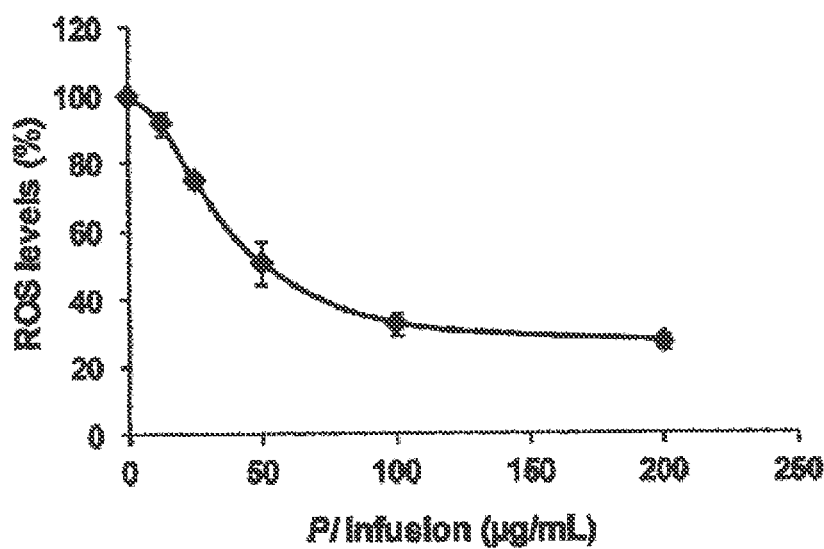

Example 22. Peroxyl Radical-Induced Oxidation of DCFH to DCF in Primary Microglial Cells, and the Inhibition of Oxidation by Pi Infusion Microglial cells were incubated for 1 h with Pi infusion. They were then preloaded with DCF-DA for 30 min and washed with PBS, after which, 0.6 mM ABAP was added and ROS levels were measured at the indicated time points. FIG. 30A; Pi infusion at 100 μg/mL. FIG. 30B: ROS levels were measured 20 h after the addition of ABAP. Each point represents mean±SEM of 2 experiments (n=8). FIG. 30 shows that peroxyl radical-induced oxidation of DCFH to DCF in primary microglial cells is inhibited by Pi infusion.

All patents, patent publications, and non-patent publications cited in the present application are incorporated by reference herein.

What is claimed is:

1. A method for treating inflammatory conditions comprising administering to an individual in need thereof a *Pulicaria incisa* (Pi) infusion for targeting microglial cells at a concentration sufficient to: 1) cause the down regulation of microglial cells activation, and 2) protect the microglial cells from oxidizing species.

2. The method according to claim 1 wherein said down regulation of microglial cells activation includes down-regulating IL-6 levels in the targeted microglial cells.

3. The method according to claim 1 wherein said down regulation of microglial cells activation includes down-regulating IL-1β levels in the targeted microglial cells.

4. The method according to claim 1 wherein said down regulation of microglial cells activation includes down-regulating glutamate levels in the targeted microglial cells.

5. The method according to claim 1 wherein said down regulation of microglial cells activation includes attenuating glutamate secretion in the targeted microglial cells.

6. The method according to claim 5 wherein said glutamate is secreted from cells including the targeted microglial cells.

7. The method according to claim 1 wherein said down regulation of microglial cells activation includes preventing glutamate-induced neuronal cell death.

8. The method according to claim 1 wherein said Pi infusion is in a form selected from a group consisting of functional food, functional beverage and/or medicinal food.

9. The method according to claim 1 wherein said Pi infusion is in a form of nutraceutical or botanical drug.

10. The method according to claim 1 wherein said Pi infusion is prepared from a wild Pi plant.

11. The method according to claim 1 wherein said Pi infusion is prepared from a cultivated Pi plant.

* * * * *